US009328060B2

(12) United States Patent
Van Dross et al.

(10) Patent No.: US 9,328,060 B2
(45) Date of Patent: May 3, 2016

(54) J-SERIES PROSTAGLANDIN-ETHANOLAMIDES AS NOVEL THERAPEUTICS

(71) Applicant: East Carolina University, Greenville, NC (US)

(72) Inventors: Rukiyah T. Van Dross, Winterville, NC (US); Daniel A. Ladin, Winterville, NC (US); Colin S. Burns, Greenville, NC (US); Allison Stokes Danell, Winterville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 14/517,239

(22) Filed: Oct. 17, 2014

(65) Prior Publication Data

US 2015/0111969 A1 Apr. 23, 2015

Related U.S. Application Data

(60) Provisional application No. 61/892,644, filed on Oct. 18, 2013.

(51) Int. Cl.
| | | |
|---|---|---|
| *A61K 9/00* | (2006.01) | |
| *A61K 31/5575* | (2006.01) | |
| *A61K 45/06* | (2006.01) | |

(Continued)

(52) U.S. Cl.
CPC ............ *C07C 235/78* (2013.01); *A61K 31/5575* (2013.01); *C07C 405/0041* (2013.01); *C07C 2101/10* (2013.01)

(58) Field of Classification Search
None
See application file for complete search history.

(56) References Cited

U.S. PATENT DOCUMENTS

| 5,981,586 A | 11/1999 | Pershadsingh |
|---|---|---|
| 6,031,001 A | 2/2000 | Stjernschantz et al. |

(Continued)

FOREIGN PATENT DOCUMENTS

| EP | 0098141 A2 | 1/1984 |
|---|---|---|
| EP | 0172963 A1 | 3/1986 |

OTHER PUBLICATIONS

Kuc et al. Arachidonoyl ethanolamide (AEA)-induced apoptosis is mediated by j-series prostaglandins and is enhanced by fatty acid amide hydrolase (FAAH) blockade. Molecular Carcinogenesis, 51: 139-149, 2012.*

(Continued)

*Primary Examiner* — Anna Pagonakis
(74) *Attorney, Agent, or Firm* — Myers Bigel Sibley & Sajovec, P.A.

(57) ABSTRACT

Provided is a compound of formula (I):

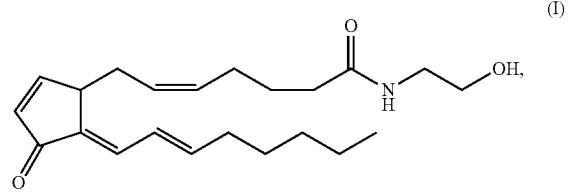

a pharmaceutical composition comprising the compound of formula (I), a pharmaceutical composition comprising anandamide (AEA) and methods of using the same in the treatment of non-melanoma skin cancer (NMSC) and colorectal cancer.

11 Claims, 18 Drawing Sheets

(51) Int. Cl.
*C07C 235/78* (2006.01)
*C07C 405/00* (2006.01)

(56) References Cited

U.S. PATENT DOCUMENTS

| 6,830,882 | B1 | 12/2004 | Evans et al. |
| 2010/0137270 | A1 | 6/2010 | Wülfert |
| 2012/0082659 | A1 | 4/2012 | Land et al. |

OTHER PUBLICATIONS

Davidson et al. "Eicosapentaenoic acid suppression of systemic inflammatory responses and inverse up-regulation of 15-deoxy$\Delta^{12, 14}$, Prostaglandin $J_2$ production", *British J. Pharmacology* 169:1130-1139 (2013).

Glass et al. "Misidentification of prostamides as prostaglandins", *J. Lipid Research* 46:1364-1368 (2005).

Li et al. "15-Deoxy$\Delta^{12, 14}$-prostaglandin $J_2$ induces growth inhibition, cell cycle arrest and apoptosis in human endometrial cancer cell lines", *Int. J. Molecular Medicine* 31:778-788 (2013).

Lin et al. "The glutathionylation of p65 modulates NF-κB activity in 15-deoxy$\Delta^{12, 14}$-prostaglandin $J_2$-treated endothelial cells", *Free Radical Biology & Medicine* 52:1844-1853 (2012).

Prage et al. "Observation of Two Modes of Inhibition of Human Microsomal Prostaglandin E Synthase 1 by the Cyclopentenone, 15-deoxy$\Delta^{12, 14}$-Prostaglandin $J_2$", *Biochemistry* 51(11):2348-2356 (2012).

Ross et al. "Pharmacological Characterization of the Anandamide Cyclooxygenase Metabolite: Prostaglandin $E_2$ Ethanolamide", *J. Pharmacology and Exp. Therapeutics* 301(3):900-907 (2002).

Soliman et al. "Anandamide is metabolized by Cyclooxygenase-2 to ethanolamide conjugate of J-series prostaglandins and induces endoplasmic reticulum stress in tumorigenic keratinocytes" *Carolina Cannabinoid Conference Abstract* 1 page. (2013).

Soliman et al. "Cyclooxygenase-2 Regulates Anandaminde-Induced Endoplasmic Reticulum Stres in Tumorigenic Keratinocytes", *American Association for Cancer Research Annual Meeting Abstract* 1 page. (2013) http://www.abstractsonline.com/Plan/ViewAbstract.aspx?mID=3086&sKey=47d150a2-0c18-41e2-aeeb-ccb249909524&cKey=7e13a39d-b13e-4de7-a0c8-179c2d78ec62&mKey=9b2d28e7-24a0-466f-a3c9-07c21f6e9bc9.

Woodward et al. "Prostamides (prostaglandin-ethanolamides) and their pharmacology", *British J. Pharmacology* 153:410-419 (2008).

\* cited by examiner

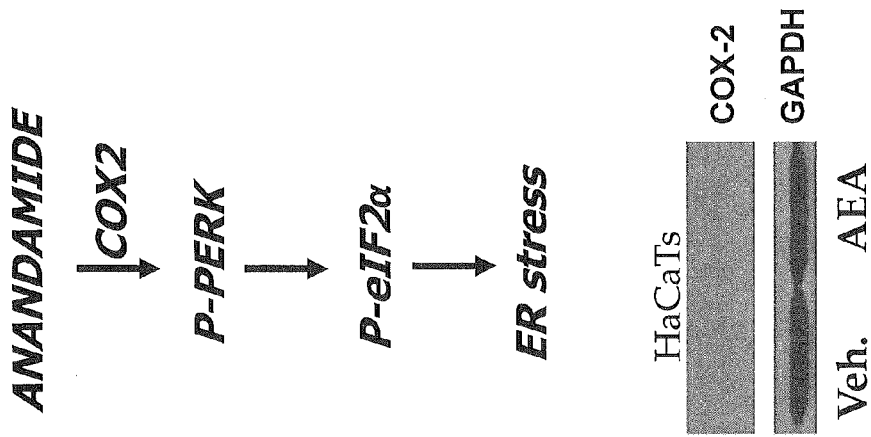
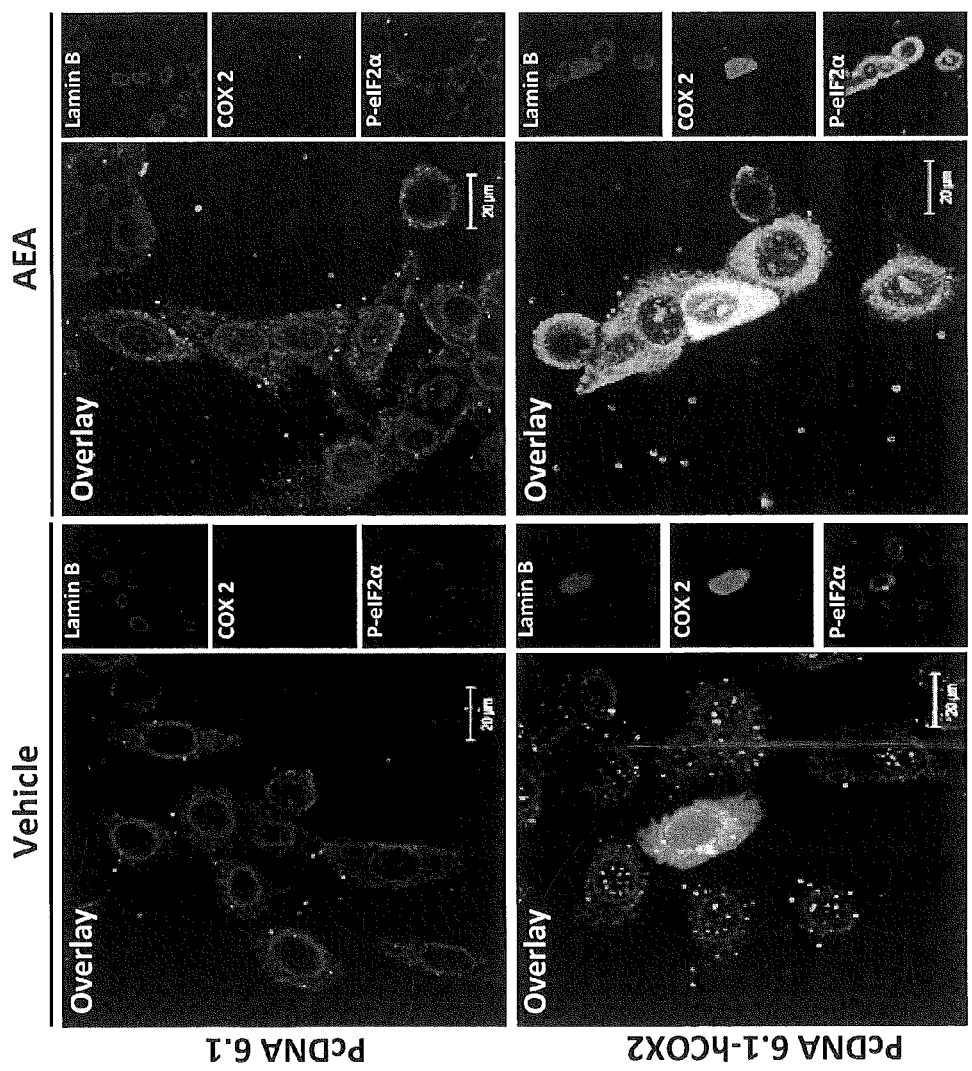
FIG. 2

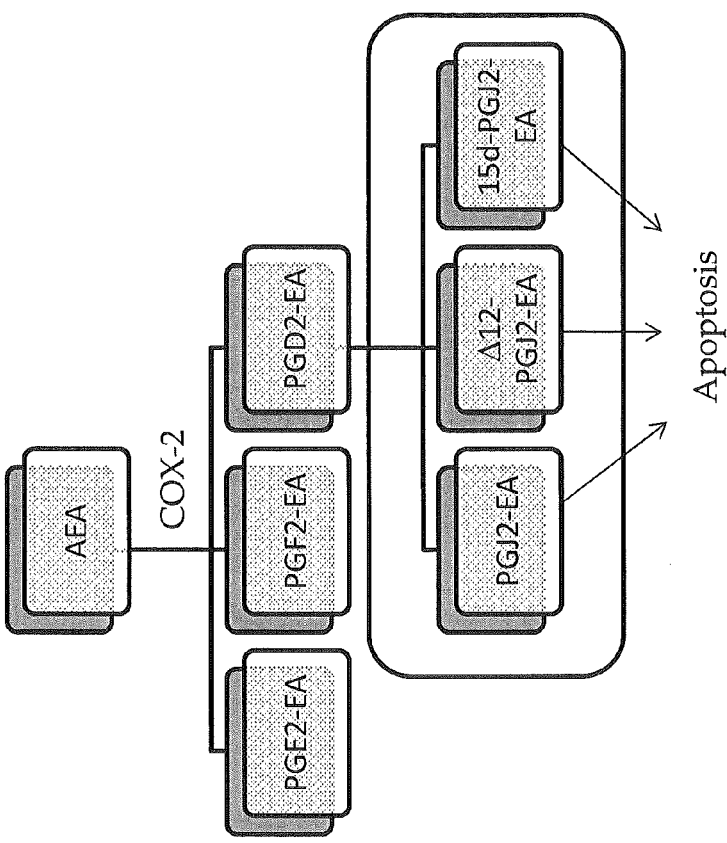
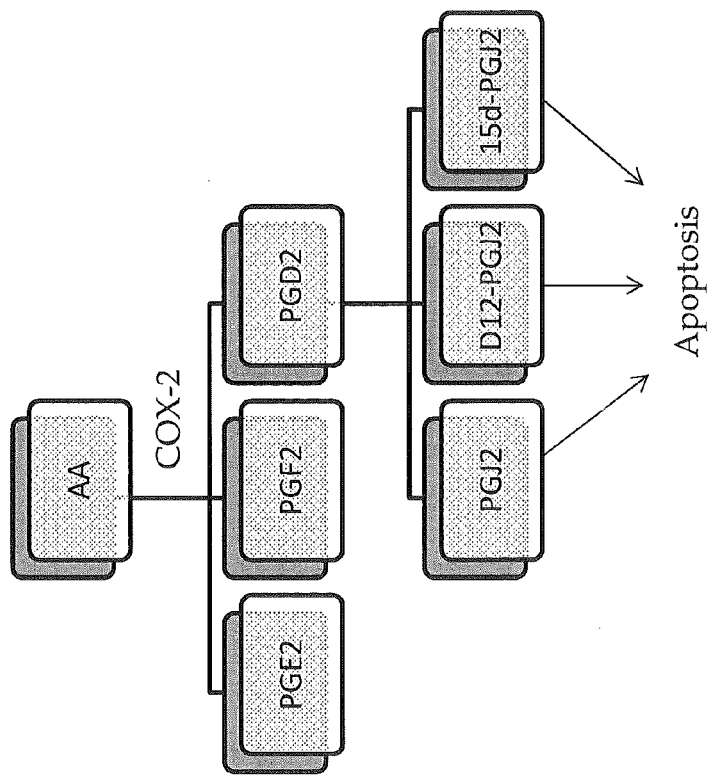
FIG. 4

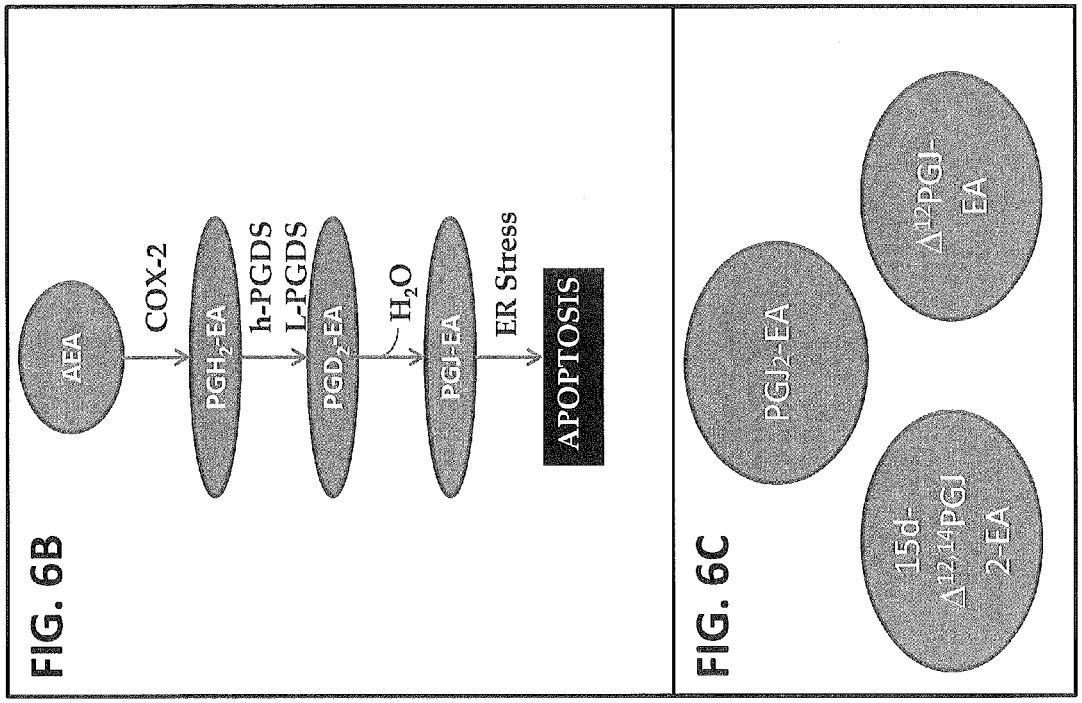
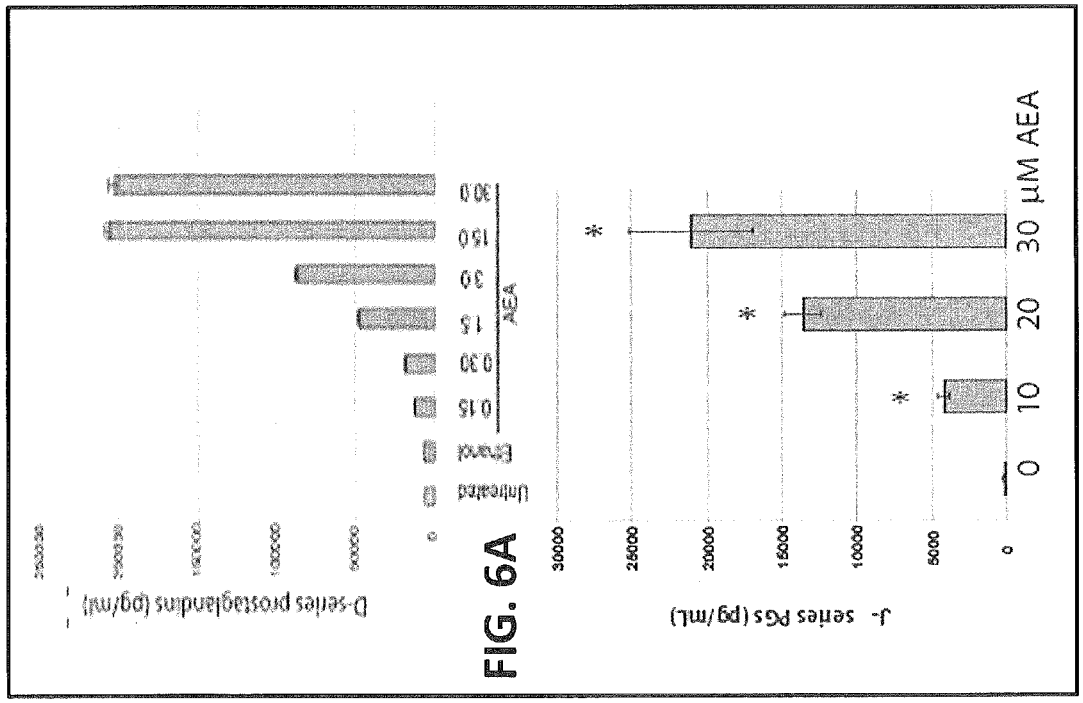

J-SERIES PROSTAGLANDIN-ETHANOLAMIDES AS NOVEL THERAPEUTICS

RELATED APPLICATIONS

This application claims the benefit of, and incorporates herein by reference in its entirety U.S. Provisional Application No. 61/892,644, filed Oct. 18, 2013. The content of which is incorporated herein by reference in its entirety.

FIELD OF THE INVENTION

The present invention relates to novel therapeutics and pharmaceutical compositions including J-series prostaglandin-ethanolamides, and methods of using and administering the same.

BACKGROUND OF THE INVENTION

There are two major types of skin cancer, non-melanoma skin cancer (NMSC) and melanoma. NMSC includes basal cell carcinoma (BCC) and squamous cell carcinoma (SCC). Together, new cases of BCC and SCC are diagnosed in more than 2 million individuals each year. Skin cancer is most commonly caused by excessive sun exposure and occupational chemical exposure. Individuals who are at increased risk of developing NMSC include the elderly, outdoor workers, outdoor sport enthusiast and organ transplant recipients. NMSC is also important due to its financial impact on our heath care system with a calculated direct cost of 1.4 billion dollars in 2004.

Nonmelanoma skin cancer is the most prevalent cancer in the United States with ~1.25 million new cases diagnosed each year. Excessive exposure to solar radiation is a common cause of NMSC. These tumors, which arise from basal and squamous keratinocytes, comprise the most common cancer in the United States and are nearly equivalent in incidence to all other forms of cancer combined. NMSC is typically treated with topical 5-fluorouracil (5FU) and/or by surgical excision. Although these techniques can be effective for eliminating skin cancer they can also produce significant damage to the surrounding non-tumor cells. As such, novel treatments and improved prevention strategies are clearly needed to address this issue. Recently, there has been a great deal of interest in determining if cannabinoids (CBs) can be developed as chemotherapeutic agents for NMSC by identifying molecular pathways targeted by these compounds. CBs are signaling lipids that are involved in processes such as pain, inflammation, appetite control, learning/memory, and drug addiction. The prototypic exogenous CB, $\Delta^9$-tetrahydrocannabinol ($\Delta^9$-THC), is the active component in marijuana. Arachidonyl ethanolamide (AEA) or anandamide is the prototypic endogenous CB (endocannabinoid) and its effects mimic those of $\Delta^9$-THC. Since the identification of AEA, other endocannabinoids have been identified including 2-arachidonoyl glycerol (2-AG), oleoyl ethanolamide (OEA), and the anti-inflammatory lipid, palmitoyl ethanolamide (PEA). Exogenous and endogenous CBs elicit biological responses by binding to and activating CB receptors 1 and 2 (CB1 and CB2) or the vanilloid receptor (VR1). CBs are then transported into cells via the anandamide membrane transporter (AMT) and its action terminated by amidases including fatty acid amide hydrolase (FAAH) or monoacylglyceride lipase (MAGL).

The utility of CBs in tumor prevention was first recognized where oral administration of $\Delta^9$-THC was shown to reduce Lewis lung adenocarcinoma growth. The endocannabinoid-induced reduction in tumor growth shown may be mediated by components of the CB system. For example, epidermal tumor growth was blocked by the synthetic CB1/CB2 receptor agonist, WIN-55, 212-2. The VR1 receptor was shown to be critical for endocannabinoid induction of cell death via a $Ca^{2+}$ sensitive mechanism. Cellular FAAH levels are also an important determinant of endocannabinoid-induced cell death at least because overexpression of FAAH protected cells from AEA-mediated cell death while genetic deletion of FAAH increased their susceptibility to cell killing. Thus, it appears that cellular proteins capable of modulating endocannabinoid action play a role in its ability to induce cell death.

Another cellular protein that is indicated to be involved in endocannabinoid-induced cell death is cyclooxygenase-2 (COX-2). COX-2 expression, as well as PG levels, is commonly elevated in NMSC and other epithelial tumors. COX-2 metabolizes arachidonic acid to prostaglandins, which promote growth and survival of tumor cells. These prostaglandins include E-, F-, D- and J-type prostaglandins. COX-2 also metabolizes endocannabinoids to form prostaglandin-ethanolamides (PG-EA). COX-2 metabolizes AEA to ethanolamide conjugated prostaglandins E, F, and D. However, J-series PG-ethanolamides have never been described previously.

AEA has been shown to induce cell death in the COX-2 overexpressing squamous carcinoma cell line JWF2. In contrast, AEA does not induce cell death in HaCaT keratinocytes, which express low basal levels of COX-2. Resistance to AEA-mediated cell death in HaCaT cells was reversed by overexpressing COX-2 in these cells. Prostaglandins have been identified to be involved in AEA-mediated cell death. D-type prostaglandins were predominantly formed in AEA-exposed JWF2 cells although significant increases in E- and F-type prostaglandins were also seen. Cells treated with various prostaglandins or PG-EA to examine AEA-induced cell death indicated that $PGD_2$ and $PGD_2$-EA are cytotoxic to JWF2 keratinocytes and that $PGD_2$ dehydration products, $PGJ_2$ and 15-deoxy $\Delta^{12,14}$ $PGJ_2$, were also inducers of cell death.

SUMMARY OF THE INVENTION

Most cancer chemotherapeutic agents kill tumor cells and cause damage to nontumor cells leading to serious and sometimes life threatening adverse effects. The compounds and compositions of the invention can overcome this problem by exploiting biochemical differences between tumor and nontumor cells. Moreover, topical drug application directly to the tumor and/or surrounding area will also aid in decreasing damage to nontumor cells. The compounds and compositions of the invention can also be effective when applied subsequent to surgical tumor removal (adjuvant therapy). It can also be useful against multifocal tumors or tumors that cannot be surgically removed due to their location on the skin.

In an aspect of the invention, provided is a compound, 15-deoxy$\Delta^{12,14}$-prostagladin $J_2$-ethanolamide (15-deoxy $\Delta^{12,14}PGJ_2$-EA), of formula (I), or a derivative thereof, and salts thereof:

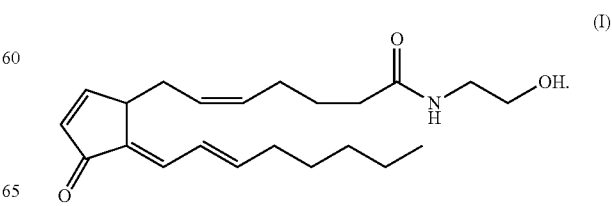

In another aspect of the invention, provided is a pharmaceutical composition comprising a therapeutically effective amount of 15-deoxy $\Delta^{12,14}$PGJ$_2$-EA, or a derivative thereof, and salts thereof, and a pharmaceutically acceptable carrier.

In yet another aspect of the invention, provided is a method of treating NMSC comprising administration of a pharmaceutical composition comprising a therapeutically effective amount of 15-deoxy $\Delta^{12,14}$PGJ$_2$-EA, or a derivative thereof, and salts thereof, to a subject in need thereof.

In yet another aspect of the invention, provided is a method of treating psoriasis comprising administering a pharmaceutical composition comprising a therapeutically effective amount of 15-deoxy $\Delta^{12,14}$PGJ$_2$-EA, or a derivative thereof, and salts thereof, to a subject in need thereof.

In yet another aspect of the invention, provided is a method of treating a colon cancer, a rectal cancer or a colorectal cancer comprising administering a pharmaceutical composition comprising a therapeutically effective amount of 15-deoxy $\Delta^{12,14}$PGJ$_2$-EA, or a derivative thereof, and salts thereof, to a subject in need thereof.

In yet another aspect of the invention, provided is a method of treating NMSC comprising administering a pharmaceutical composition comprising a therapeutically effective amount of AEA, or a derivative thereof, and salts thereof, to a subject in need thereof.

In other aspects of the invention, treating NMSC refers to treating basal cell carcinoma (BCC), squamous cell carcinoma (scc), Kaposi's sarcoma, cutaneous lymphoma, skin adnexal tumors, sarcomas, or Merkel cell carcinoma and combinations thereof.

In yet another aspect of the invention, provided is a method of treating a colon cancer, a rectal cancer or a colorectal cancer comprising administering a pharmaceutical composition comprising a therapeutically effective amount of AEA, or a derivative thereof, and salts thereof to a subject in need thereof.

In further embodiments, methods of the present invention relate to preventing the disorders described herein using a therapeutically effective amount of 15-deoxy $\Delta^{12,14}$PGJ$_2$-EA, or a derivative thereof, and salts thereof and/or a therapeutically effective amount of AEA, or a derivative thereof, and salts thereof to a subject.

Embodiments of the present invention also provide kits comprising the compounds and/or compositions described herein and a container suitable for housing or delivery of the compounds and/or composition within a common packaging, and instructions for use of the same.

BRIEF DESCRIPTION OF THE DRAWINGS

FIG. 2 shows AEA-induced ER stress is COX-2 dependent.

FIG. 4 shows products of AEA metabolism by COX-2 may regulate its cytotoxicity.

FIGS. 6A-6C show AEA induces cell death due to its metabolism by COX-2 to D-series PGs which are then converted to J-series PGs which induce ER stress and apoptosis. FIG. 6A shows AEA causes a concentration-dependent increase in D- and J-series PG synthesis. FIG. 6B depicts the scheme for ER stress-induced apoptosis through COX-2 metabolism of AEA. FIG. 6C shows the metabolic products of AEA metabolism by COX-2.

DETAILED DESCRIPTION

Figure 1:
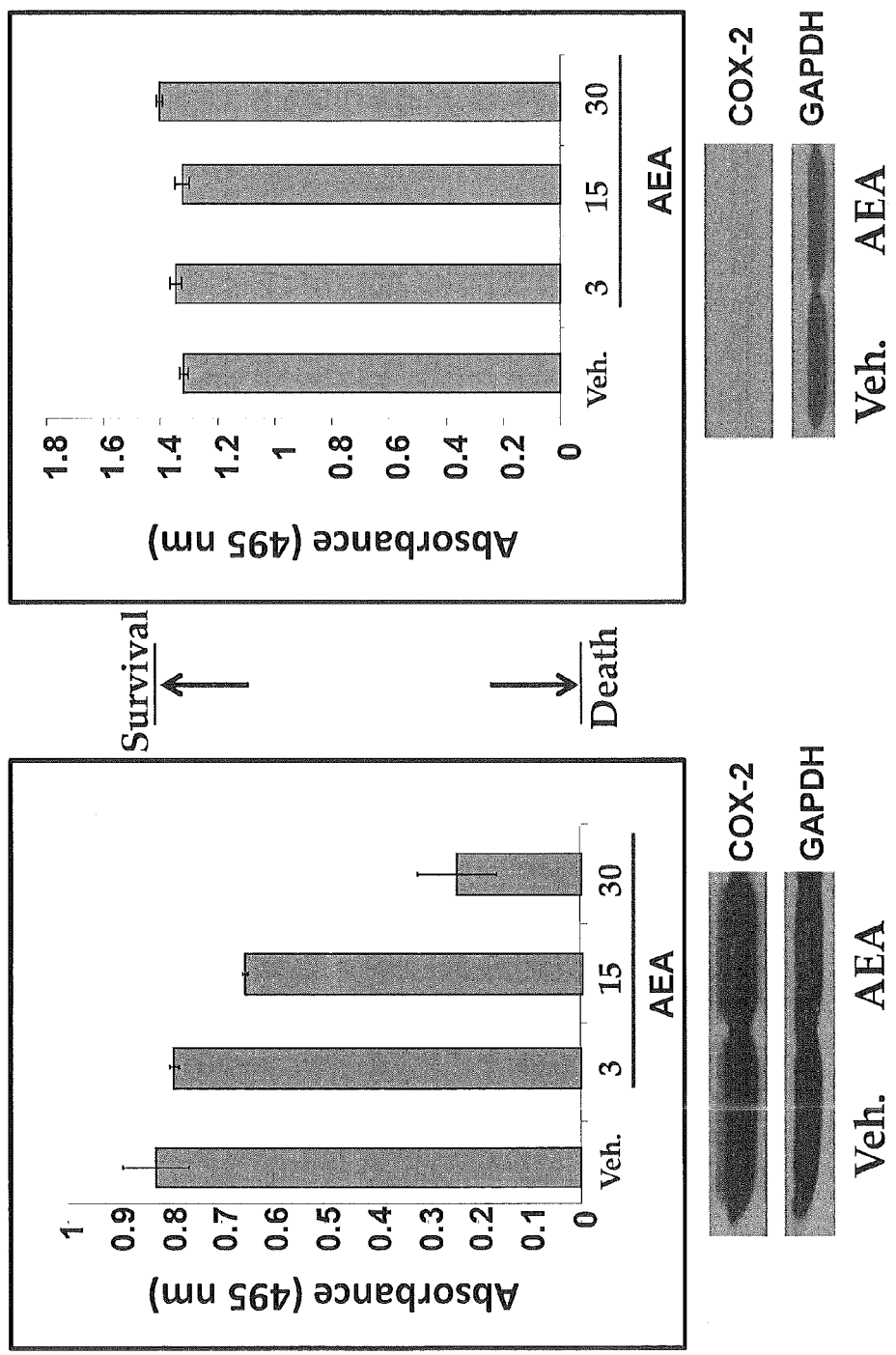
FIG. 1 shows AEA induces cell death in diseased, but not healthy cells.

In the following detailed description, embodiments of the present invention are described in detail to enable practice of the invention. Although the invention is described with reference to these specific embodiments, it should be appreciated that the invention can be embodied in different forms and should not be construed as limited to the embodiments set forth herein. Rather, these embodiments are provided so that this disclosure will be thorough and complete, and will fully convey the scope of the invention to those skilled in the art. All publications cited herein are incorporated by reference in their entireties for their teachings.

The invention includes numerous alternatives, modifications, and equivalents as will become apparent from consideration of the following detailed description.

As used herein, the singular forms "a," "an" and "the" are intended to include the plural forms as well, unless the context clearly indicates otherwise. For example, "a" cell can mean one cell or a plurality of cells.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims or figures unless specifically indicated otherwise.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz*, 537 F.2d 549, 551-52, 190 USPQ 461, 463 (CCPA 1976) (emphasis in the original); see also MPEP §2111.03.

As used herein, "one or more" can mean one, two, three, four, five, six, seven, eight, nine, ten or more, up to any number.

Unless otherwise defined, all technical terms used herein have the same meaning as commonly understood by one of ordinary skill in the art to which this disclosure belongs.

The term "administering" or "administered" as used herein is meant to include topical, parenteral and/or oral administration, all of which are described herein. Parenteral administration includes, without limitation, intravenous, intraperitoneal, subcutaneous and/or intramuscular administration (e.g., skeletal muscle or cardiac muscle administration). In the methods of this invention, the compound or composition of this invention may be administered alone and/or simultaneously with one or more other compounds. In some embodiments, the compounds may be administered sequentially, in any order. It will be appreciated that the actual method and order of administration will vary according to, inter alia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, topical, rectal, intraperitoneal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

As used herein, the terms "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent," "preventing," or "prevention of" (and grammatical variations thereof) refer to prevention and/or delay of the onset and/or progression of a metabolic disease in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

"Nonmelanoma skin cancer" or "NMSC" is the most common form of skin cancer. Basal cell carcinoma (BCC) and squamous cell carcinoma (SCC) are the most common forms of nonmelanoma skin cancers. Other nonmelanoma skin cancers are less common skin cancers and include Kaposi's sarcoma, which usually starts within the deeper layers of the skin but can also form in internal organs and can occur in people with compromised immune systems; cutaneous lymphoma, a type of lymphoma that begins in the skin; skin adnexal tumors that may start in the hair follicles or sweat glands; sarcomas, which usually start in tissues deep beneath the skin, but can develop in the skin; and Merkel cell carcinoma, that may develop on or just beneath the skin and in hair follicles.

"15-deoxy $\Delta^{12,14}PGJ_2$-EA," "15dD12,14-PGJ-EA" or "15d-PGJ-EA" refer to 15-deoxy $\Delta^{12,14}$-prostagladin $J_2$-ethanolamide as set forth in formula (I):

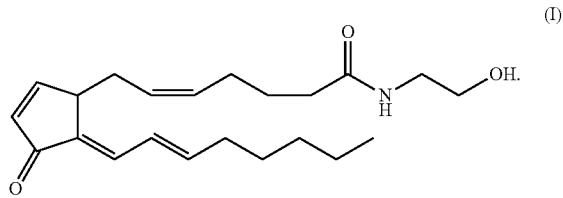 [SMILES: CCCCC/C=C/C=C1/C(=O)C=CC1C/C=C\CCCC(=O)NCCO]

(I)

"AEA" or "anandamide" refer to arachidonoyl ethanolamide as set forth in formula (II):

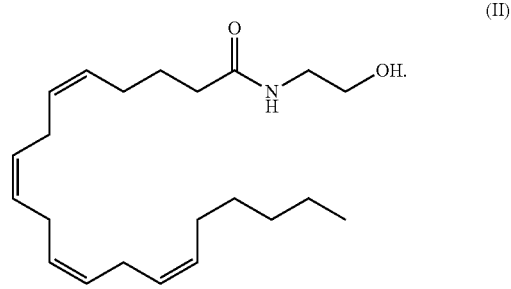 [SMILES: CCCCC/C=C\C/C=C\C/C=C\C/C=C\CCCC(=O)NCCO]

(II)

"Salt" or "pharmaceutically acceptable salt" as used herein refers to a salt that retains the biological effectiveness of the free acids and bases of a specified compound and is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propionates, oxalates, malonates, succinates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates. In particular embodiments, the salt is a hydrochloride, sulfite, benzoate, salicykate, cocoate, tallowate, undecylenate or carboxylate salt.

Compositions

The present invention is based on the discovery of 15-deoxy $\Delta^{12,14}PGJ_2$-EA and its ability to selectively cause tumor cell apoptosis by inducing endoplasmic reticulum (ER) stress. Tumor cells contain moderate levels of ER stress due to the high demand for newly synthesized proteins needed for uncontrolled proliferation. In contrast, non-tumor cells contain low levels of ER stress. When tumor cells are exposed to ER stress inducing agents the total level of ER stress exceeds the death threshold leading to apoptosis. However, when non-tumor cells are exposed to the same concentration of an ER stress inducing drug the total ER stress level may not exceed the death threshold leading to selective killing of tumor cells.

In an embodiment of the invention, provided is a compound of formula (I) or a derivative thereof, and salts thereof. This compound may be prepared according to any method that is within the grasp of one of skill in the art.

Another embodiment of the invention provides a pharmaceutical composition, comprising a therapeutically effective amount of the compound of formula (I) or a derivative thereof, and salts thereof. In a further embodiment, the pharmaceutical composition comprises a therapeutically effective amount of AEA or a derivative thereof. In yet another embodiment, the pharmaceutical composition comprises AEA and a fatty acid amide hydrolase (FAAH) inhibitor. Examples of FAAH inhibitors include, but are not limited to, PMSF (phenylmethylsulfonylfluoride), MAFO, ATMK (arachidonoyltrifluoromethylketone), URB597, urea-based inhibitors such as PF-622 and PF750, other compounds such as PF 3845, TC-F 2, LY 2183240, PF750, JNJ 1661010, SA 57 and RN-450 29.

In yet another embodiment, the pharmaceutical composition further comprises a pharmaceutically acceptable carrier. The term "pharmaceutically acceptable carrier" as used herein refers to any substance, not itself a therapeutic agent, used as a vehicle for delivery of a therapeutic agent to a subject. Non-limiting examples of pharmaceutically acceptable components include, without limitation, any of the standard pharmaceutical carriers such as phosphate buffered saline solutions, water, emulsions such as oil/water emulsions or water/oil emulsions, microemulsions, and various types of wetting agents. Further, in preparing such pharmaceutical compositions comprising the active ingredient or ingredients in admixture with components necessary for the formulation of the compositions, other conventional pharmacologically acceptable additives may be incorporated, for example, excipients, stabilizers, antiseptics, wetting agents, emulsifying agents, lubricants, sweetening agents, coloring agents, flavoring agents, isotonicity agents, buffering agents, antioxidants and the like. As the additives, there may be mentioned, for example, starch, sucrose, fructose, dextrose, lactose, glucose, mannitol, sorbitol, precipitated calcium carbonate, crystalline cellulose, carboxymethylcellulose, dextrin, gelatin, acacia, EDTA, magnesium stearate, talc, hydroxypropylmethylcellulose, sodium metabisulfite, and the like.

Although the derivatives of the compounds of the invention are not particularly limited, an exemplary embodiment of the derivatives of the compound of formula (I) or AEA of the invention are more poorly absorbed in the gastrointestinal (GI) tract of a subject.

The pharmaceutical compositions of the present invention may be suitably formulated for administration by any means known in the art. Non-limiting examples of forms of administration include, but are not limited to oral, parenteral (e.g., subcutaneous, intravenous, intramuscular, intra-articular, intra-synovial, intrasternal, intrathecal, intrahepatic, intralesional and intracranial injection or infusion techniques), inhalation spray (nasal and oral), topical (i.e., both skin and mucosal surfaces, including airway surfaces), transdermal, rectal, nasal, sublingual, buccal, or implanted reservoir administration, etc. In one embodiment, the compositions are administered topically or transdermally. For topical administration, suitable forms include, but are not limited to, suitable transdermal delivery systems known in the art, such as patches, and for nasal delivery, suitable forms include, but are not limited to, aerosol and nebulized delivery systems known in the art In a particular embodiment, pharmaceutical compositions of the present invention may be in the form suitable for topical administration. Non-limiting examples include pharmaceutical compositions in the form of a topical solution, ointment, cream, emulsion, a gel, a dispersion, a suspension, a foam, an aerosol, a droplet, an injectable form and/or a coating in which the active component may be suspended or dissolved in one or more carriers. A topical composition may be applied to body surfaces of a subject, including skin, mucous membranes, scalp, hair and/or nails. Carriers for topical administration of the compounds of this invention include, but are not limited to, mineral oil, liquid petrolatum, white petrolatum, propylene glycol, polyoxyethylene, polyoxypropylene compound, emulsifying wax and water. Where the topical formulation is in the form of an ointment or cream, suitable carriers include, but are not limited to, mineral oil, sorbitan monostearate, polysorbate 60, cetyl esters wax, cetearyl alcohol, 2 octyldodecanol, benzyl alcohol and water.

In other embodiments, pharmaceutical compositions may include excipients that include at least one viscosity agent, at least one solvent and at least one humectant. The term excipient refers to "inert" constituents of pharmaceutically acceptable compositions. The term "inert" indicates that such constituents are not considered active pharmaceutical ingredients, such as antimicrobial compounds, anti-inflammatory agents, pain-relievers, immunosuppressants and vasodilators. However, as one of ordinary skill in the art will understand, the excipients may provide beneficial or therapeutic action (e.g., moisturize, provide anti-inflammatory effects). The excipients may also indirectly affect the treatment of topical ailments by affecting the stability of active pharmaceutical ingredients (APIs), wherein the API is a compound according to formula (I), AEA or a derivatives thereof, within the compositions. In a particular embodiment, a fatty acid amide hydrolase (FAAH) inhibitor is added to the pharmaceutical composition. It will be understood that any suitable combination of excipients may be present in the pharmaceutical compositions described herein.

Excipients for use in topical formulations are well-known in the art and examples may be found in the Handbook of Pharmaceutical Excipients (Rowe, R. C. et al., APhA Publications; 5th ed., 2005). Classes of excipients may include waxes, emollients, thickening agents/viscosity increasing agents, humectants, pH modifiers, water repelling agents, anti-foaming agents, surfactants, solubilizers, wetting agents, penetration enhancers, antioxidants, and solvents. The excipients may also be present in the topical composition at any suitable concentration. In some embodiments, the topical composition includes excipients at a concentration in a range from 70 to 99.99 weight percent.

Any suitable viscosity increasing agent may be used, and combinations of viscosity increasing agents may also be used. In some embodiments of the invention, the polymeric portion of the viscosity increasing agent may act as a visco-elastic substance and may retain the gel at the site of application, along with the APIs dispersed therein. Examples of viscosity increasing agents include co-polymers of carboxymethylcellulose and acrylic acid, N-vinylpyrrolidone, polyalkylene glycols (e.g., poly(ethylene glycol)), polyalkylene oxides (e.g., polyethylene oxide), polyvinyl alcohols, polyvinylpyrrolidone, polysiloxanes, poly(vinyl acetates), cellulose, derivatized celluloses, alginates, copolymers thereof and blends thereof. A specific example of a viscosity agent is hydroxypropylcellulose, such as Klucel® hydroxypropylcellulose (e.g., Klucel® MF Pharm grade).

Any suitable solvent, or combinations of solvents may be used in the topical compositions. Examples of solvents include acetone, methyl alcohol, ethanol, isopropanol, butyl alcohol, ethyl acetate, dimethyl isosorbide, propylene glycol, glycerol, ethylene glycol, polyethylene glycol, diethylene glycol monoethyl ether or mixtures thereof. In particular examples, the solvent includes ethanol. In some embodiments, the solvent includes isopropyl alcohol. The skilled artisan will appreciate that the solvents may also be considered excipients, particularly at lower concentrations.

Any suitable humectant or combination of humectants may be used. Examples include glycols, such as diethylene glycol monoethyl ether; glycerols; sugar polyols, such as sorbitol, xylitol and maltitol; polyols such as polydextroses; quillaia, urea, and blends thereof. In particular examples, the humectant includes an alkylene glycol, such as hexylene glycol.

Methods of formulating pharmaceutical compositions have been described in numerous publications such as Pharmaceutical Dosage Forms: Tablets. Second Edition. Revised and Expanded. Volumes 1-3, edited by Lieberman et al.; Pharmaceutical Dosage Forms: Parenteral Medications. Volumes 1-2, edited by Avis et al.; and Pharmaceutical Dosage Forms Disperse Systems. Volumes 1-2, edited by Lieberman et al.; published by Marcel Dekker, Inc, the disclosure of each of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

In some embodiments, the compounds provided by the present invention comprises a lower limit ranging from about 0.01, 0.02, 0.03, 0.04, 0.05, 0.06, 0.07, 0.08, 0.09, 1.0, 2.0, 3.0, 4.0, 5.0, 6.0, 7.0, 8.0, 9.0, and 10% to an upper limit ranging from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% by weight of the composition.

Methods of Administration and Use

Another embodiment of the present invention provides a method for administering to a subject in need thereof a compound or pharmaceutical composition as described herein. For administration, either the compound or pharmaceutical composition is understood as being the active ingredient and capable of administration to a subject, and thus, in some instances, the terms are interchangeable. Non-limiting methods of administration include, but are not limited to oral, parenteral (e.g., subcutaneous, intramuscular, intradermal, intraperitoneal, or intravenous), inhalation spray (nasal and oral), topical (i.e., both skin and mucosal surfaces, including airway surfaces), transdermal, rectal, nasal, sublingual, buccal, or implanted reservoir administration, etc. In one embodiment, the compositions are administered, topically or transdermally. In a particular embodiment, the compositions are administered topically. In yet another embodiment, the compositions are administered intraperitoneally.

In another embodiment of the present invention, provided is a method of treatment or prevention of a medical condition treatable by the compounds and pharmaceutical compositions as described herein comprising administering to a subject or patient suffering from said condition (or at risk for) the compounds or pharmaceutical compositions as described herein. In still other embodiments, the medical condition is a colon cancer, rectal cancer, or colorectal cancer. Other medical conditions applicable herein include skin diseases such as those associated with cell proliferation, such as psoriasis, eczema and dermatitis (whether or not of allergic origin), and also inflammatory gastrointestinal conditions including Crohn's disease, ulcerative colitis and distal proctitis.

In still other embodiments, the method of treatment is given as primary therapy of the medical condition. In yet other embodiments, the method of treatment is given as adjuvant therapy to other methods of treatment of the medical condition.

In a particular embodiment the method of treatment comprises topical administration of the pharmaceutical composition as described herein. The method of topical administration is not particularly limited, and may be through any procedure that will be appreciated by one of skill in the art. In a further embodiment, the method of treatment comprises transdermal administration of the pharmaceutical composition as described herein. The method of transdermal administration is not particularly limited and may be through any procedure that will be appreciated by one of skill in the art. In another particular embodiment, the medical condition treatable by the pharmaceutical compositions as described herein is NMSC.

In yet another embodiment, the medical condition treatable by the pharmaceutical compositions as described herein is colon cancer. In yet a further embodiment, the medical condition treatable by the pharmaceutical compositions as described herein is psoriasis. "Psoriasis can refer to a chronic, relapsing/remitting, immune-mediated skin disease characterized by red, scaly patches, papules, and plaques, which may itch. There are generally five main types of psoriasis: plaque, guttate, inverse, pustular, and erythrodermic.

In some embodiments, the subject is administered antineoplastic chemotherapy or radiotherapy prior to, at the same time, or after receiving a compound or composition of the present invention. The antineoplastic chemotherapy can be one or more of: folate antagonists, including methotrexate and pemetrexed; purine antagonists, including cladribine, clofarabine, fludarabine, 6-mercaptopurine, nelarabine, pentostatin; pyrimidine antagonists, including capecitabine, cytarabine, 5-fluorouracil, gemcitabine, hydroxyurea; biologic response modifiers, including interferon-alfa; bleomycin; DNA alkylating agents, including nitrosureas, carmustine, lomustine; DNA cross-linking drugs and alkylating agents, including bendamustine, chlorambucil, cyclophosphamide, ifosfamide, mechlorethamine (nitrogen mustard), melphalan, dacarbazine, temozolomide, procarbazine; asparaginase; antibiotics, including mitomycin; platinum complexes, including carboplatin, cisplatin, oxaliplatin; proteosome inhibitors, including bortezomib; spindle poisons, such as the taxanes (including docetaxel, paclitaxel, nab-paclitaxel (Abraxane®)) and the vincas (including vinblastine, vincristine, vinorelbine); topoisomerase inhibitors, such as the anthracyclines (including daunorubicin, daunomycin, doxorubicin, epirubicin), the camptothecines, (including irinotecan, topotecan), the podophyllotoxins (including etoposide, teniposi de and mitoxantrone); tyrosine kinase inhibitors, (including erlotinib (Tarceva), gefitinib, imatinib, lapatinib, pazopanib, sorafenib, sunitinib); and ifosfamide.

It should also be understood that a specific dosage and treatment regimen for any particular patient will depend upon a variety of factors, including but not limited to, the age, body weight, general health, gender, diet, time of administration, rate of excretion, drug combination, and the judgment of the treating physician and the severity of the particular disease being treated.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. The human subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

A subject of this invention is any subject in whom prevention and/or treatment is needed or desired, as well as any subject prone to cancers described herein and/or psoriasis. In some embodiments, the subject is a human; however, a subject of this invention can include an animal subject, particularly mammalian subjects such as canines, felines, bovines, caprines, equines, ovines, porcines, rodents (e.g. rats and mice), lagomorphs, primates (including non-human primates), etc., for veterinary medicine or pharmaceutical drug development purposes.

Illustrative avians according to the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, and for drug screening and drug development purposes. Suitable subjects include subjects in need thereof, at risk for cancer, diagnosed with cancer and/or undergoing chemotherapy and/or subjects at risk for psoriasis diagnosed with psoriasis and/or undergoing treatment for psoriasis.

Embodiments of the present invention also provide kits including the elements necessary to carry out the therapies described above. Such a kit may comprise a carrier being compartmentalized to receive in close confinement therein one or more containers, such as tubes or vials. One or more of the containers may contain a compound described herein. One or more containers may contain one or more enzymes or reagents to be utilized in desired reactions. These enzymes may be present by themselves or in admixtures, in lyophilized form or in appropriate buffers. The kit may contain all of the additional elements necessary to carry out the methods of the invention.

It is understood that the combinations of all embodiments described herein are also envisaged in the present invention.

The present invention will now be described in more detail with reference to the following examples. However, these examples are given for the purpose of illustration and are not to be construed as limiting the scope of the invention.

EXAMPLES

Identification of a Role of 15-Deoxy $\Delta^{12,14}$-PGJ$_2$-EA in Tumor Cell Death A cannabinoid that can induce cell death in tumorigenic keratinocytes was identified. Tumorigenic JWF2 keratinocytes were treated with various concentrations of AEA and cell viability measured using MTS analysis. In FIG. 1, high absorbance indicates that cells are living while low absorbance indicates that the cells are dead. As shown in FIG. 1, AEA caused a concentration-dependent decline in tumor cell viability. In contrast we examined the effect of AEA on non-tumorigenic HaCaT keratinocytes and found that cell treatment with AEA did not lead to a loss of viability. An interesting feature of tumorigenic keratinocytes is that they overexpress COX-2. However, non-tumorigenic keratinocytes contain low basal levels of COX-2. Therefore, the role of COX-2 in the cytotoxicity of AEA was examined.

Since it was determined that AEA-induced cell death required COX-2 we examined whether ER stress also required COX-2. In this experiment we utilized HaCaT keratinocytes which express low basal levels of COX-2. The cells were transfected with an empty vector (pcDNA6.1) or an expression vector containing COX-2. In FIG. 2 the red signal indicates COX-2 expression, green indicates P-eIF2a phosphorylation and the blue stains the nuclear membrane for orientation. In AEA treated cells transfected with COX-2 a significant increase in eIF2a phosphorylation is observed relative to the corresponding empty vector transfected cells. In contrast, minimal eIF2a phosphorylation was noted in vehicle treated cells transfected with our without COX-2. These data show that AEA-induced ER stress occurs in a COX-2 dependent manner.

Figure 3:
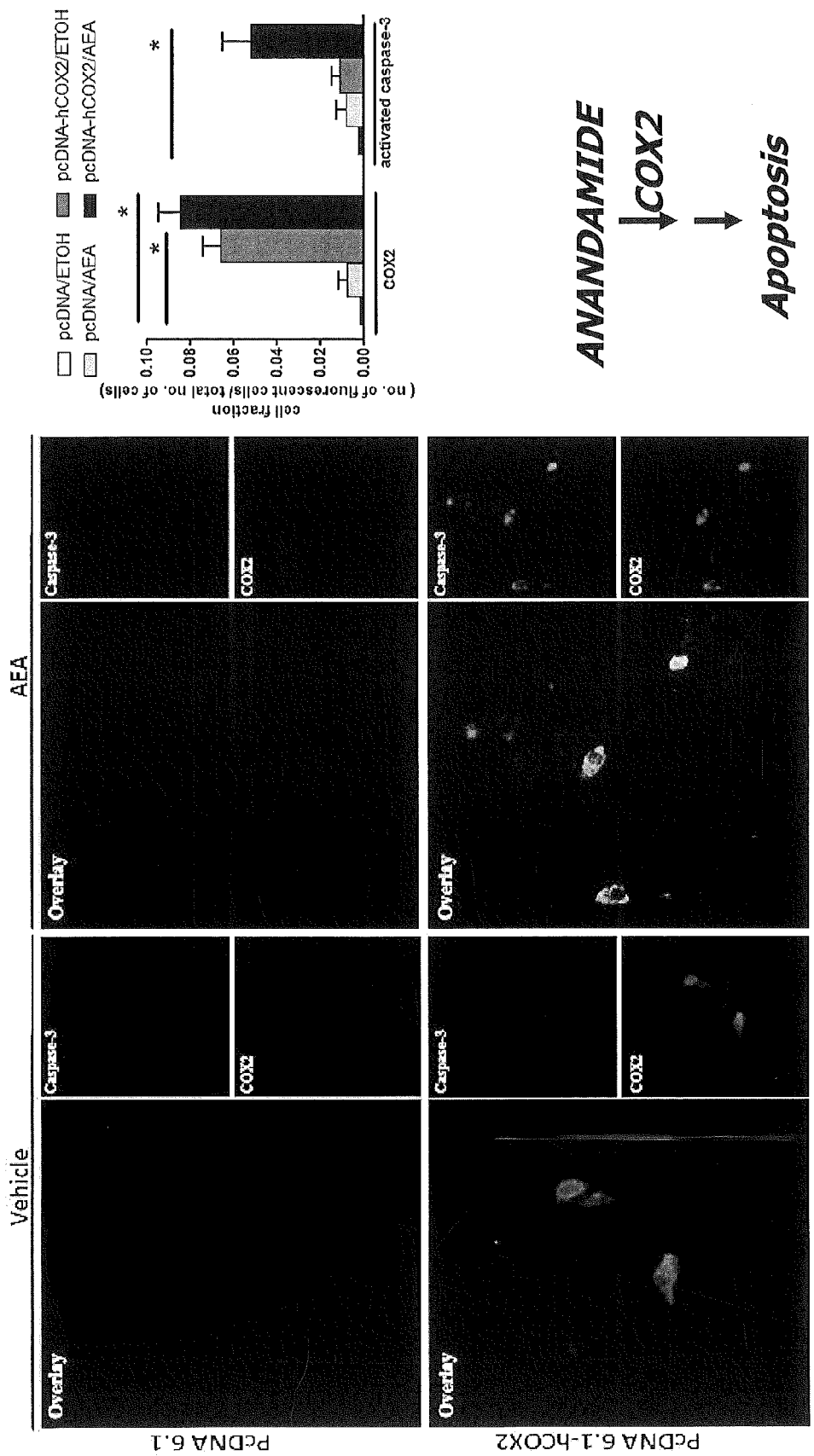
FIG. 3 shows AEA-induced apoptosis is COX-2 dependent.

Next, the requirement of COX-2 in AEA-induced apoptosis was examined and shown in FIG. 3. Red staining indicates COX-2 while the green stain indicates activated caspase-3, a hallmark for apoptosis. The data show that AEA induced apoptosis requires COX-2 since cell treated with AEA in the absence of COX-2 did not undergo apoptosis.

These data show that AEA causes ER stress and apoptosis in keratinocytes that overexpress COX-2 but not in keratinocytes that lack COX-2 expression. Since the function of COX-2 is to synthesize prostaglandins, these data suggest that a product of AEA metabolism by COX-2 plays a role in the induction of ER stress and apoptosis caused by AEA.

COX-2 metabolizes AA to prostaglandins. These prostaglandins include E-, F-, D- and J-type prostaglandins. As it turns out, COX-2 can also metabolize the endocannabinoid AEA to ethanolamide conjugated prostaglandins E, F, and D as outlined in FIG. 4. However, J-series PG ethanolamides have heretofore not been described or been available commercially. To understand which metabolic product of AEA mediates its cytotoxic effects, we purchased the arachidonic acid derived prostaglandins and the E, F, and D prostaglandin-ethanolamides. J-series PG-EAs, however, are not available commercially.

Figure 5:
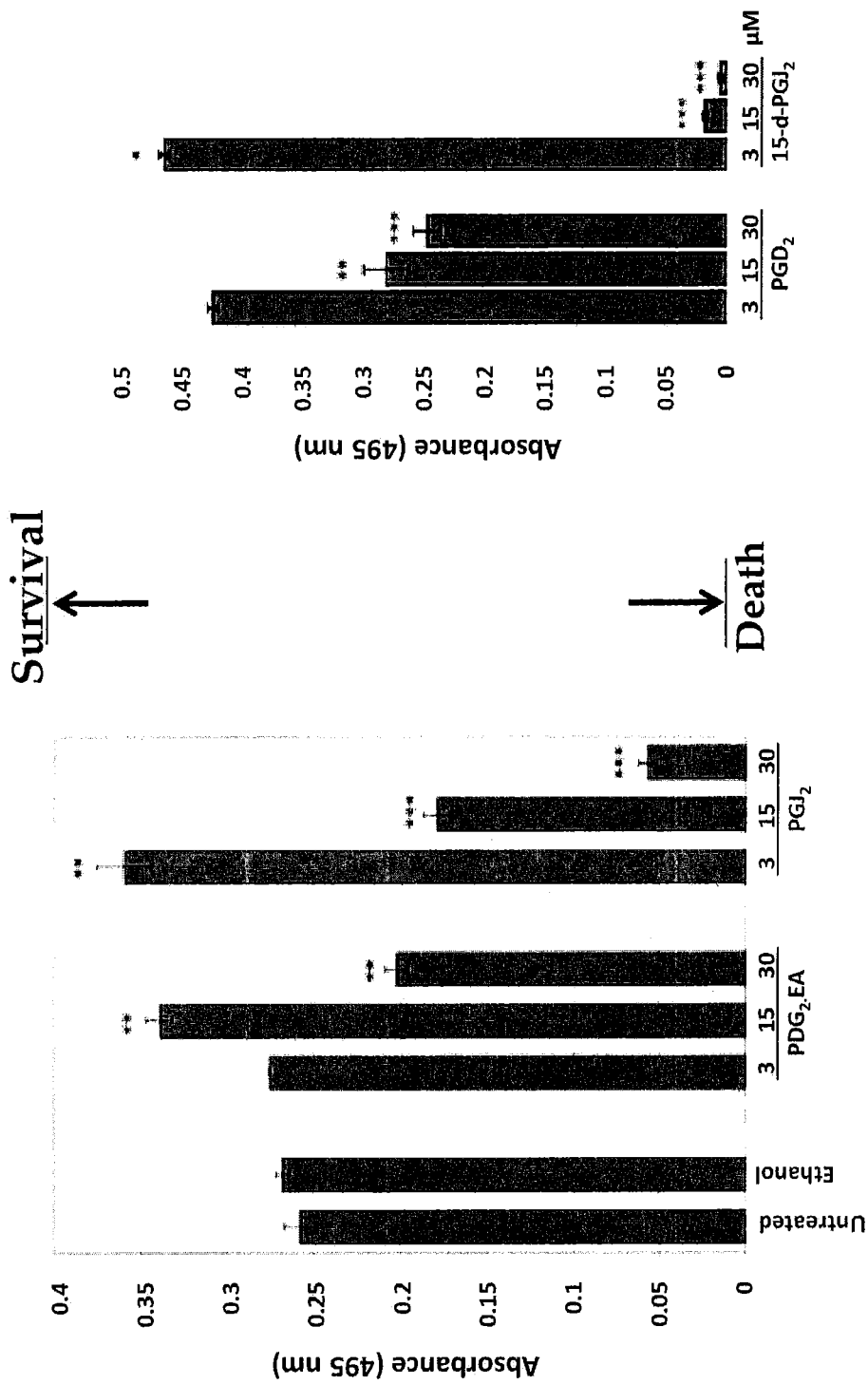
FIG. 5 shows D- and J-series PGs induce cell death in tumorigenic keratinocytes.
Figure 5:
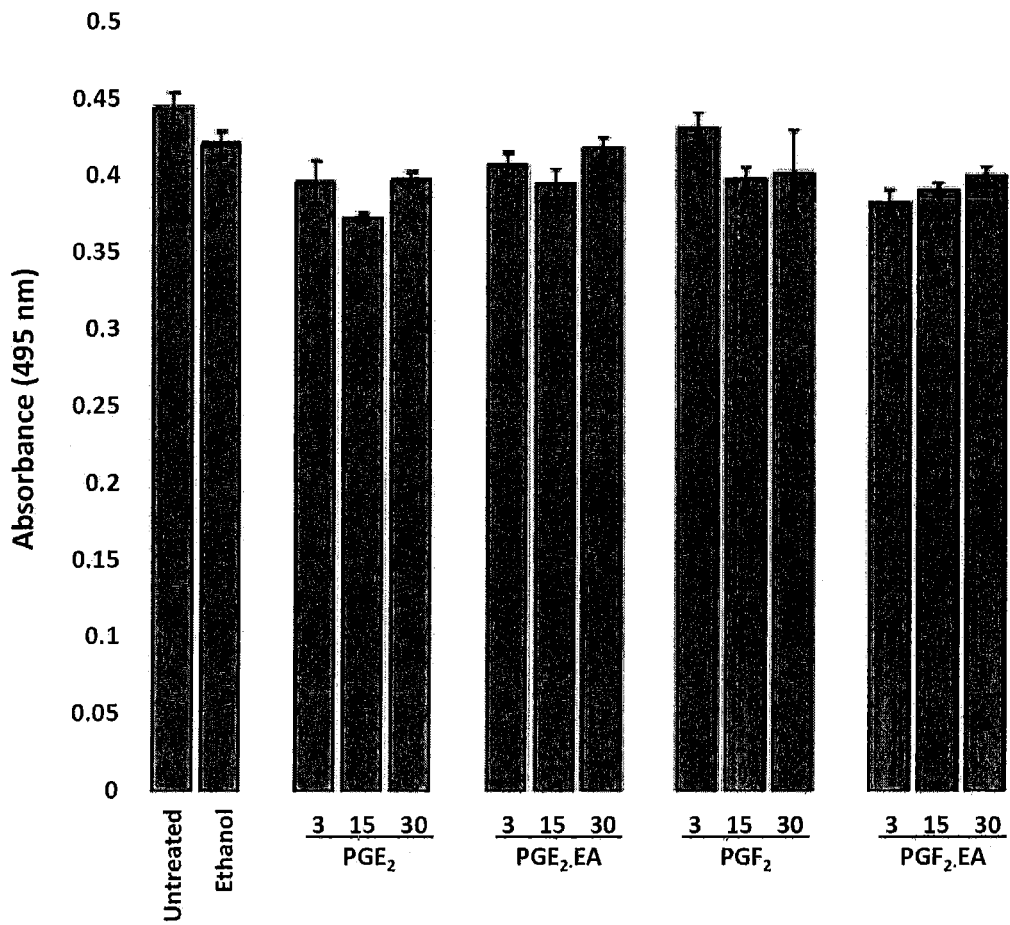

JWF2 tumorigenic keratinocytes were treated with each of these prostaglandins and cell survival measured in MTS assays. As shown in FIG. 5, only D- and J-series PGs induce cell death in tumorigenic keratinocytes.

To determine if D- and J-series PGs are synthesized endogenously, JWF2 cells were treated with various concentrations of AEA and prostaglandin synthesis measured using ELISA assays. AEA caused a concentration-dependent increase in D- and J-series PG synthesis as shown in FIG. 6A. These combined findings suggest that AEA induces cell death due to its metabolism by COX-2 to D-series PGs which are then converted to J-series PG which induce ER stress and apoptosis as shown in FIG. 6B.

To identify the specific J-series PGs that are produced in AEA-treated cells that overexpress COX-2 we treated the cells with AEA, collected the culture medium and analyzed J-series PGs using LC/MS. Our investigation showed for the first time that PGJ-EA, D12-PGJ-EA and 15dD12,14-PGJ-EA are metabolic products of AEA as shown in FIG. 6C. 15dD12,14-PGJ-EA was identified as the most abundant produced.

Figure 7:
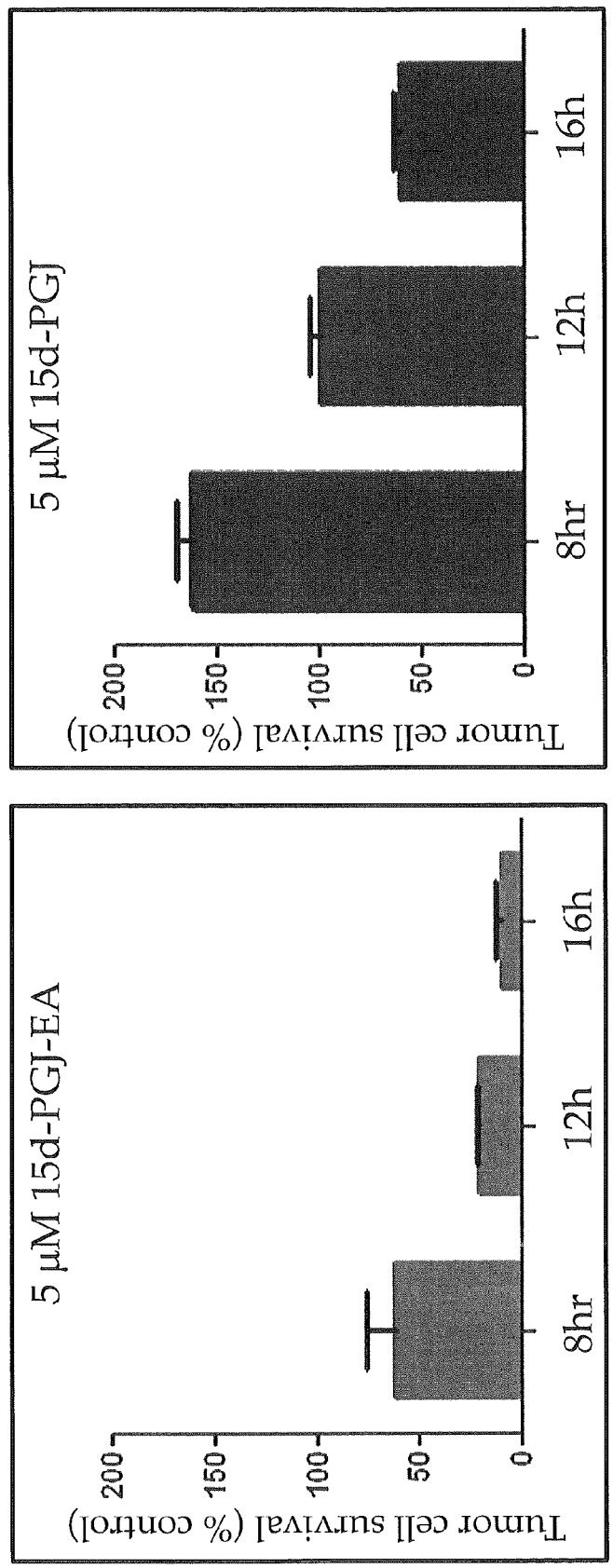
FIG. 7 shows 15d-PGJ-EA is a potent inducer of tumor cell death.

FIG. 7 shows that 15d-PGJ-EA is a potent inducer of tumor cell death, particularly as compared to 15d-PGJ.

Figure 8:
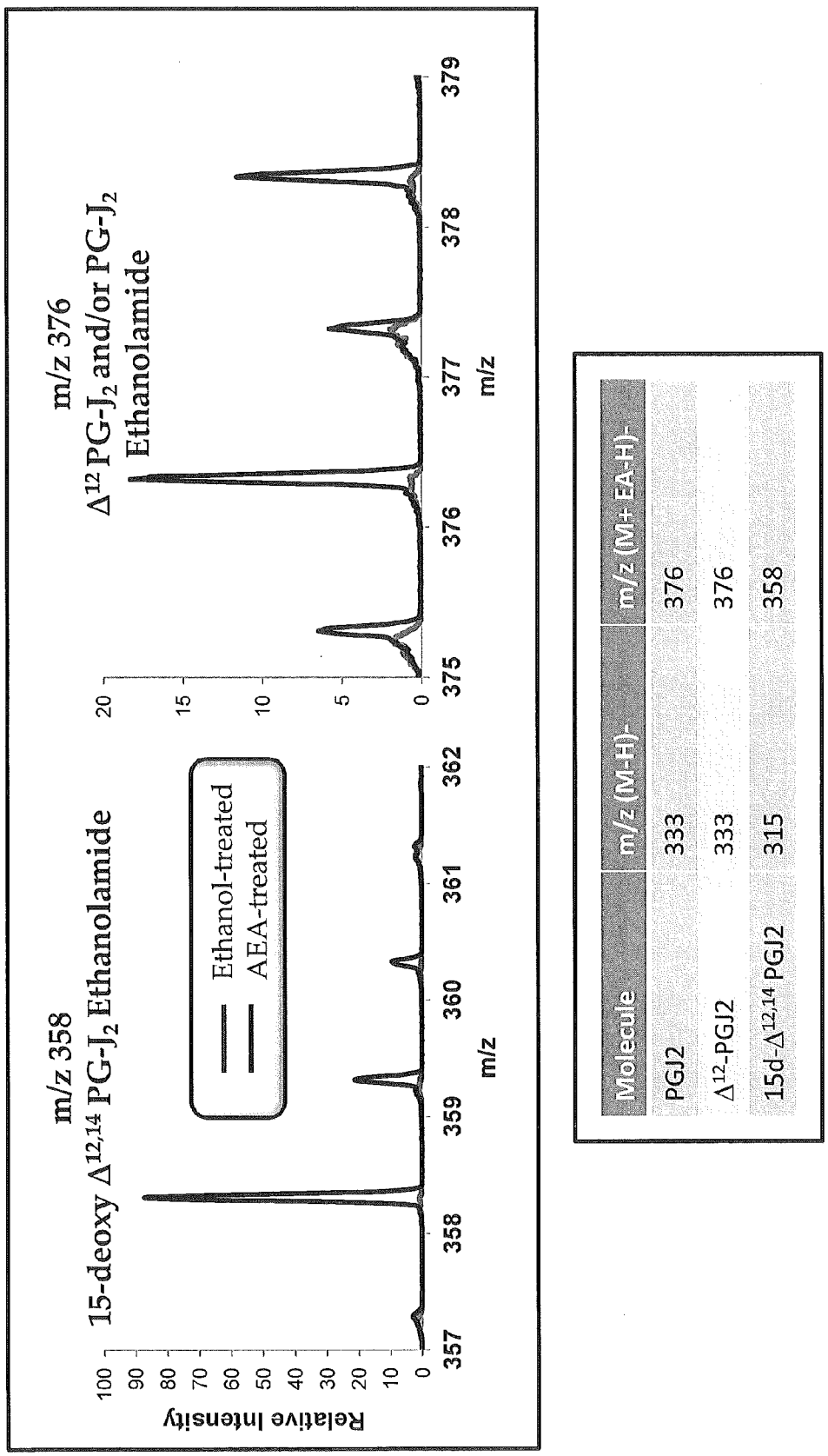
FIG. 8 shows MS signals corresponding to prostaglandins: m/z 358 for 15dD12,14-PGJ-EA and m/z 376 for PGJ2-EA and D12-PGJ-EA is detected only in AEA-treated cells.
Figure 9:
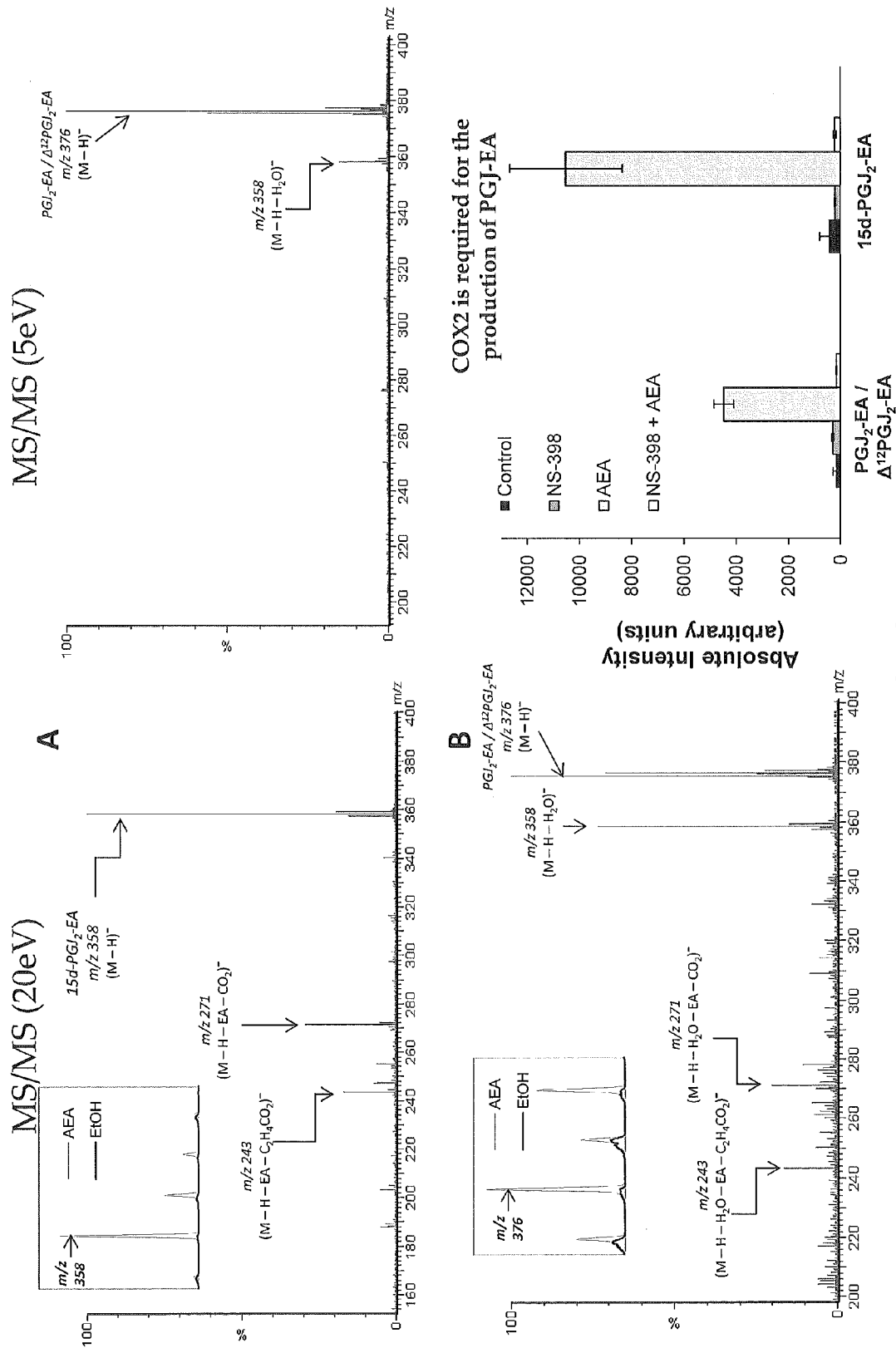
FIG. 9 shows MS/MS at high collision energy for m/z 358 and 376 peaks and that COX-2 is required for production of PGJ-EA.

15dD12,14-PGJ-EA was detected and identified only in AEA-treated cells as shown by MS as shown in FIG. 8. To confidently identify these m/z values, high collision energy MS/MS was run for m/z 358 and 376 peaks as shown in FIG. 9. LC-MS/MS spectra show peaks at m/z 358 and 376, illustrating the use of MS/MS to confidently identify these m/z values. In FIG. 9A, the MS/MS spectrum of m/z 358 is shown, in which product ions at m/z 271 (M-H-EA-CO2)$^-$ and m/z 243 (M-H-EA-C2H4CO2)$^-$ were detected and identified. The inset shows that m/z 358 was detected in LC-MS spectra of AEA-treated cells (red), but not vehicle-treated cells (blue). FIG. 9B shows the MS/MS spectrum of m/z 376, which dissociated to m/z 358 (M-H—H2O)$^-$, m/z 271 (M-H—H2O-EA-CO2)$^-$ and m/z 243 (M-H—H2O-EA-C2H4CO2)$^-$. Again, the inset shows the overlay of the LC-MS signal for the AEA-treated cells (red) and EtOH-treated cells (blue), and no significant m/z 376 peak is observed in the blue trace.

Similar MS/MS spectra are to be expected for CID of these prostaglandins because of the structural similarity of 15-deoxy Δ12,14-PGJ2-EA and PGJ2-EA or Δ12-PGJ2-EA. In addition, fragmentation of these prostaglandins is facile enough to occur during ion transmission through mass spectrometer. Because m/z 358 was observed in LC-MS spectra of AEA-treated cells as well as in LC-MS/MS spectra of m/z 376, a control experiment was conducted to approximate the extent of unintended dissociation m/z 376 and is shown in FIG. 9C. The parent ion, m/z 376, was mass-selected and subjected to CID at the same collision energy used in LC-MS (5 eV). This very low potential acts to focus the ion beam through the hexapole collision cell to obtain a conventional mass spectrum. As seen in FIG. 9C, only a low intensity m/z 358 peak is observed, indicating m/z 376 does not significantly dissociate to m/z 358 under the conditions used to obtain LC-MS spectra. The majority of the signal at m/z 358 arises from the production of 15-deoxy Δ12,14 PG-J2-EA in the AEA-treated cells.

To determine the direct role of COX-2 in AEA-induced ER stress, the requirement of COX-2 for J-series PG-ethanolamide synthesis was assessed. Results are depicted in FIG. 9D. JWF2 cells were pretreated with the selective COX-2 inhibitor NS-389, exposed to AEA or vehicle, and LC/MS conducted on the extracted cell culture medium. NS-398 prevented the synthesis of 15-deoxy, D12,14-PGJ2-EA and PGJ2/D12PGJ2-EA indicating that COX-2 is required for its synthesis.

Figure 10:
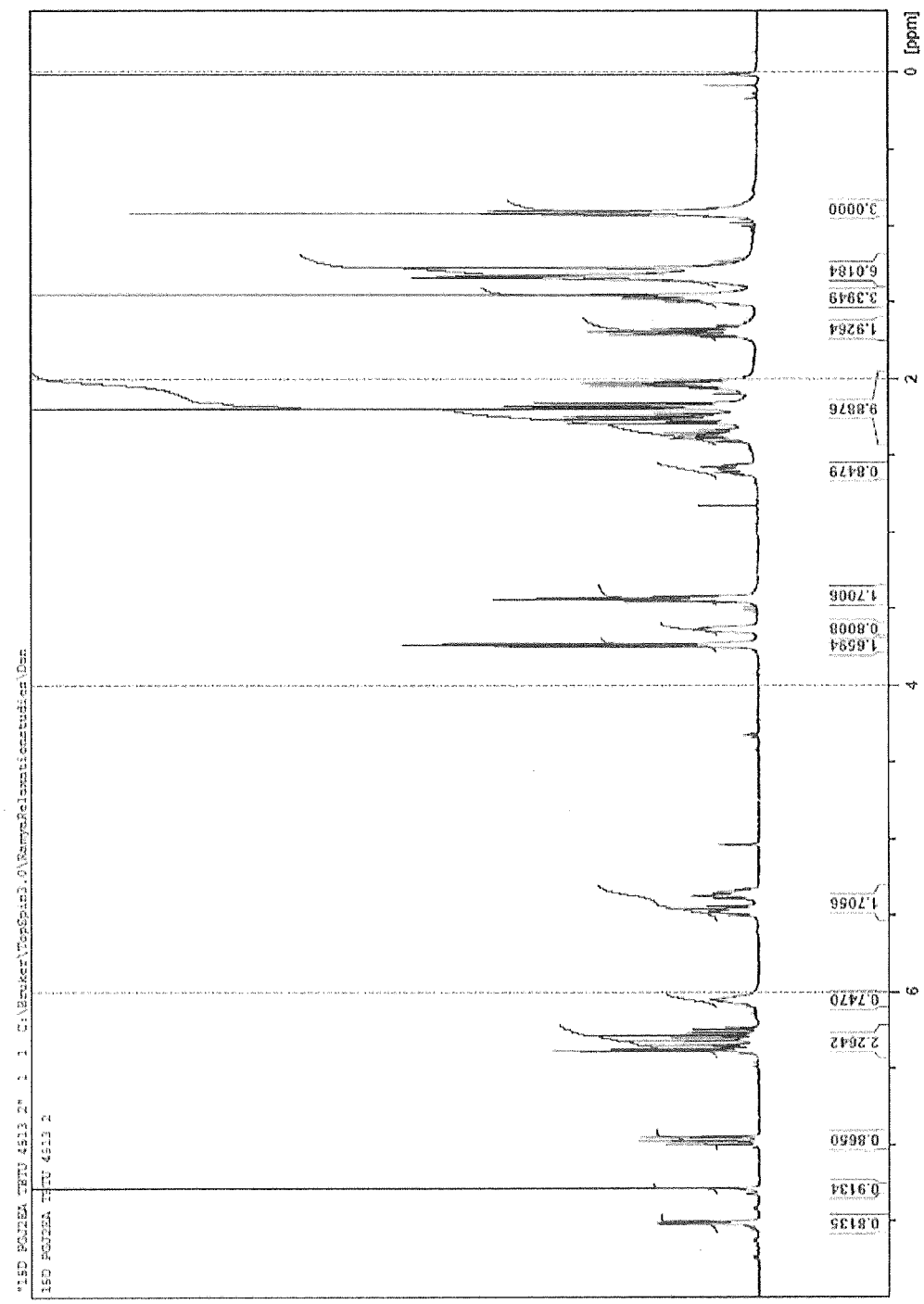
FIG. 10 shows Verification of 15dD12,14-PGJ-EA synthesis with NMR.

Synthesis of 15-Deoxy $\Delta^{12,14}$PGJ$_2$-EA 15-deoxy-$\Delta^{12,14}$-Prostaglandin J$_2$ (15-deoxy-$\Delta^{12,14}$-PGJ$_2$, Cayman Chemical, Ann Arbor, Mich.) was dissolved in a small volume of acetonitrile and approximately 1 mole equivalent of O-(Benzotriazol-1-yl)-N,N,N',N'-tetramethyluronium tetrafluoroborate (TBTU), and 4 mole equivalents of diisopropylethylamine were added. The solution was stirred for approximately 5 minutes and 2 mole equivalents of ethanolamine were added. The reaction solution was stirred for 24 hours with a brown precipitate forming. Reaction mixture was vacuum filtered and the solvent removed by rotary evaporation to yield a yellow crude product. This product was re-dissolved into ether solvent and washed three times with water. The organic phase was collected and evaporated to yield a pure faint yellow product, which was characterized by $^1$H NMR. See FIG. 10.

The Effects of AEA are Mediated by 15dPGJ-EA

Figure 11:
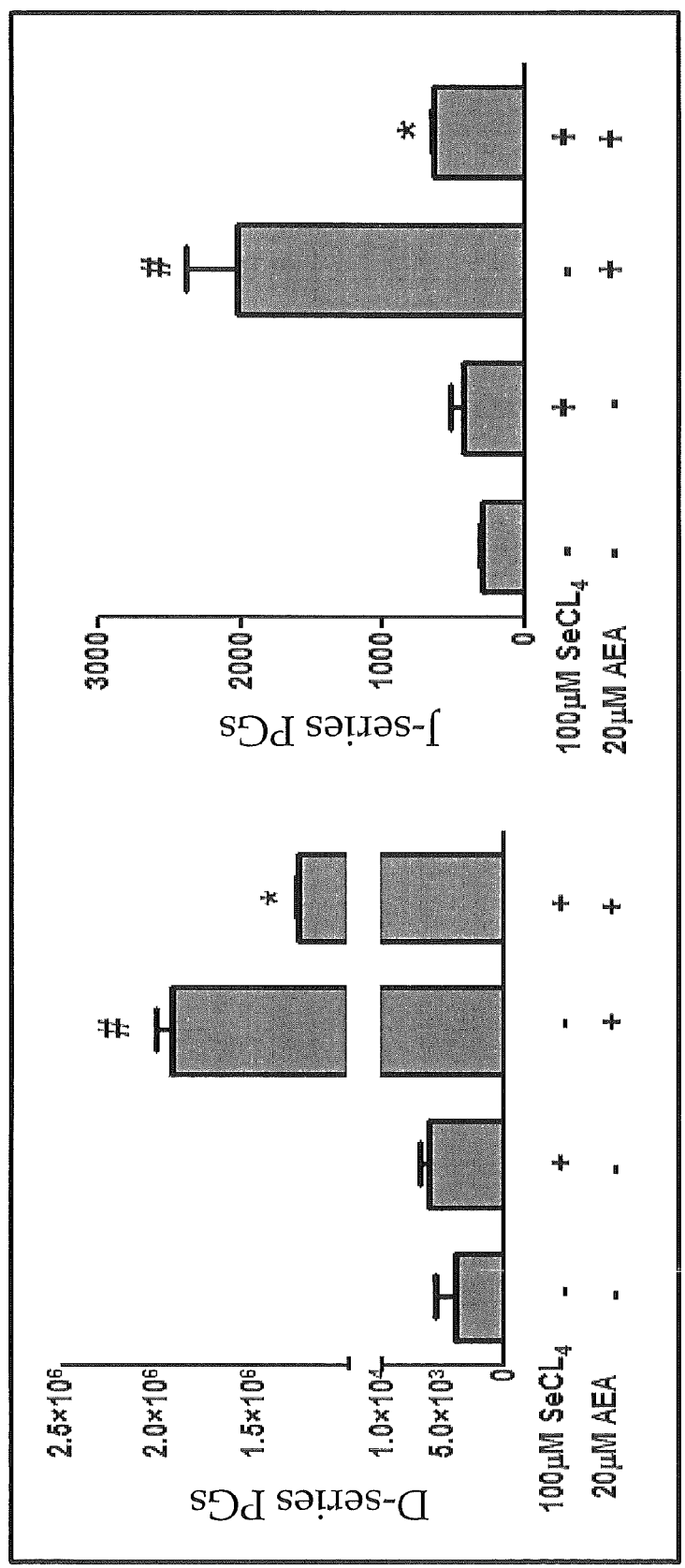
FIG. 11 shows H-PGDS and L-PGDS inhibitor "SeCL4" reversed AEA-induced PGD$_2$ and PGJ$_2$ production.
Figure 12:
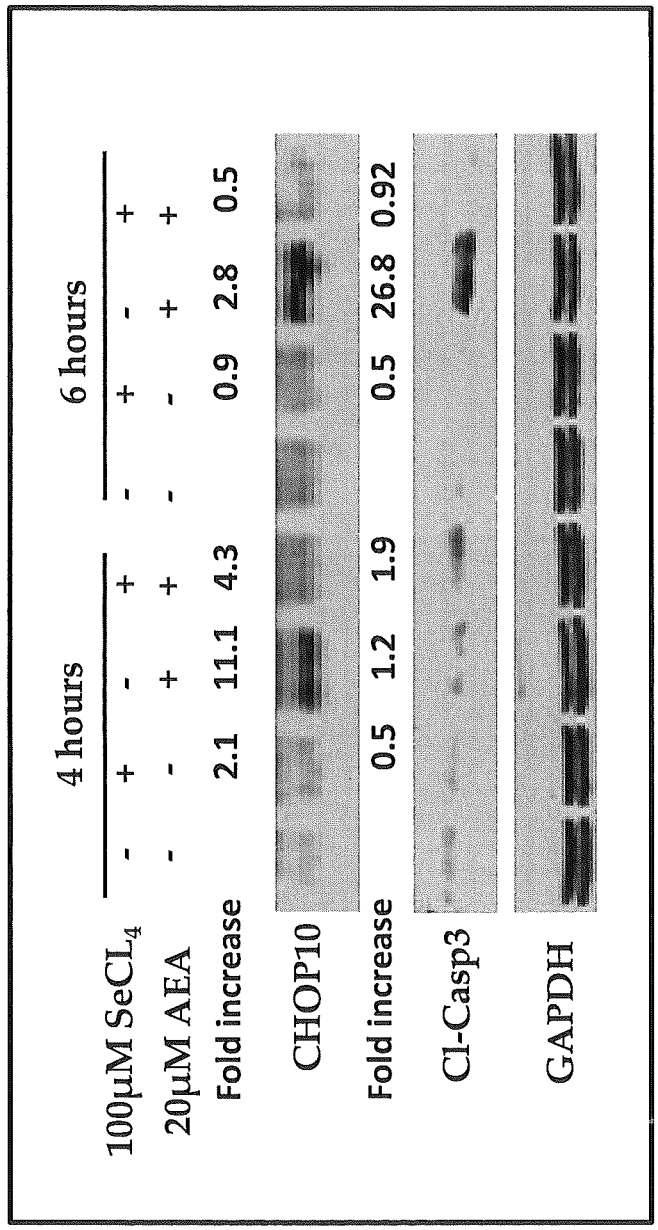
FIG. 12 shows SeCL4 inhibits AEA-induced CHOP10 expression and Caspase-3 cleavage.
Figure 13:
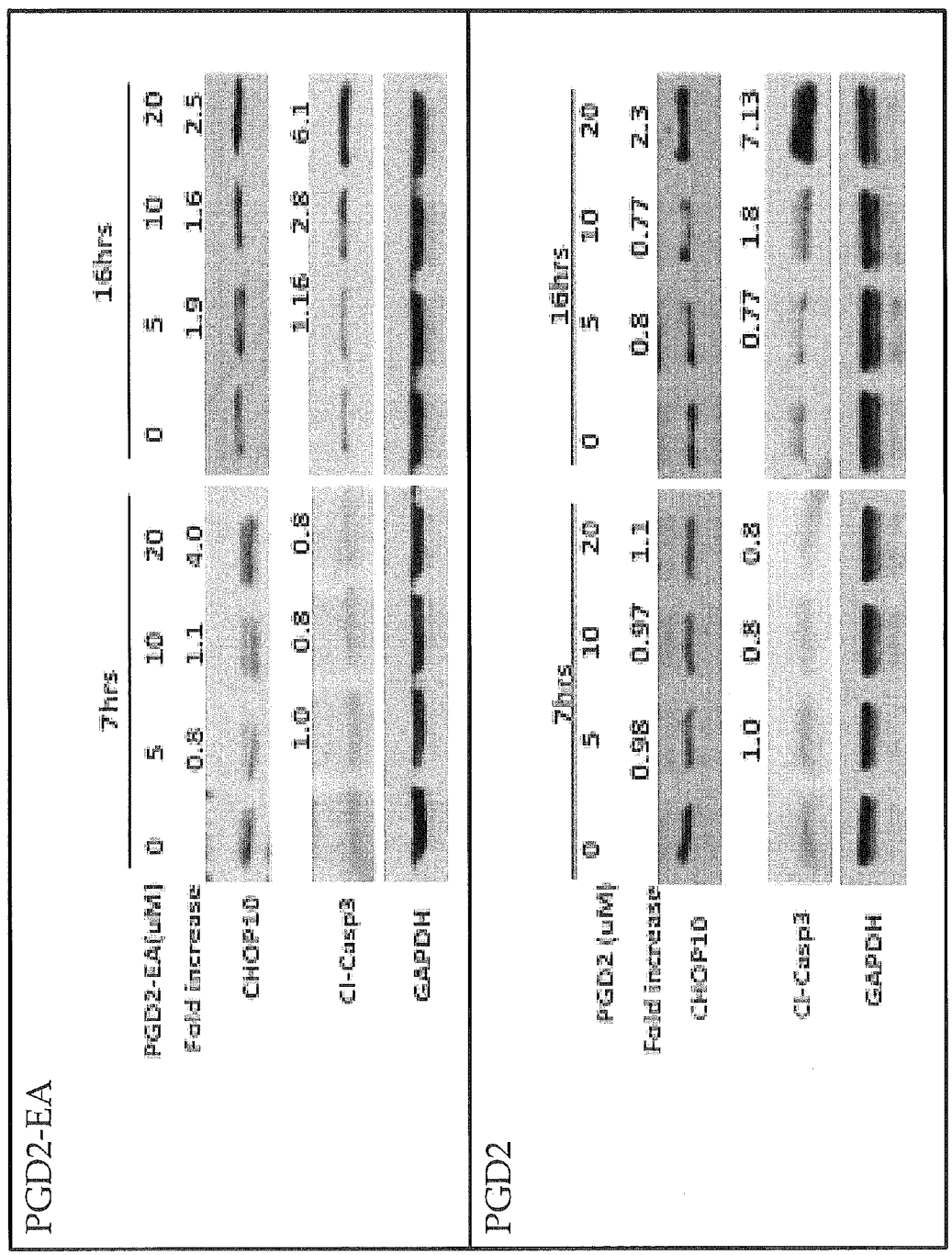
FIG. 13 shows PGD$_2$-EA increases CHOP10 expression and Cl-Casp3.
Figure 14:
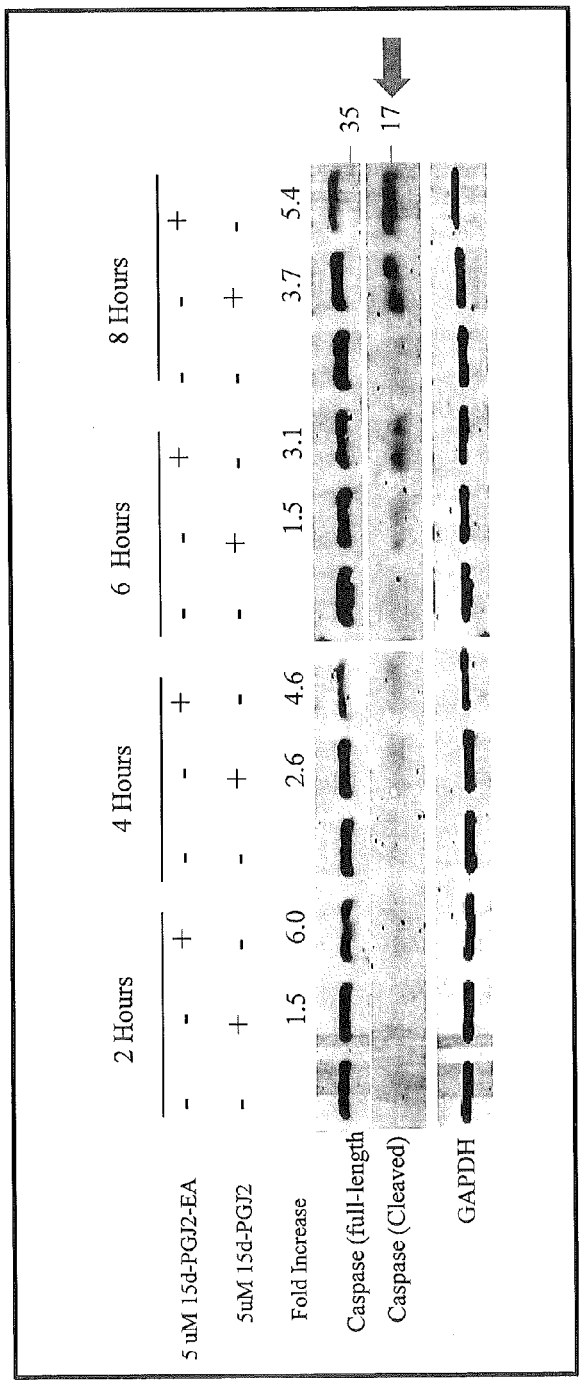
FIG. 14 shows 15dPJG-EA induces apoptosis in tumorigenic keratinocytes.

H-PGDS and L-PGDS inhibitor "SeCL4" reversed AEA-induced PGD2 and PGJ2 production as shown in FIG. 11. SeCL4 also inhibited AEA-induced CHOP10 expression and Caspase-3 cleavage, an indicator of apoptosis, as shown in FIG. 12. PGD2-EA increased CHOP10 and Cl-Casp3 expression as shown in FIG. 13. FIG. 14 shows that 15dPGJ-EA induces apoptosis in tumorigenic keratinocytes (Jwf2), but not in non-tumorigenic keratinocytes (HaCat).

15d-PGJ-EA May be Functionally Distinct from 15d-PGJ

Figure 15:
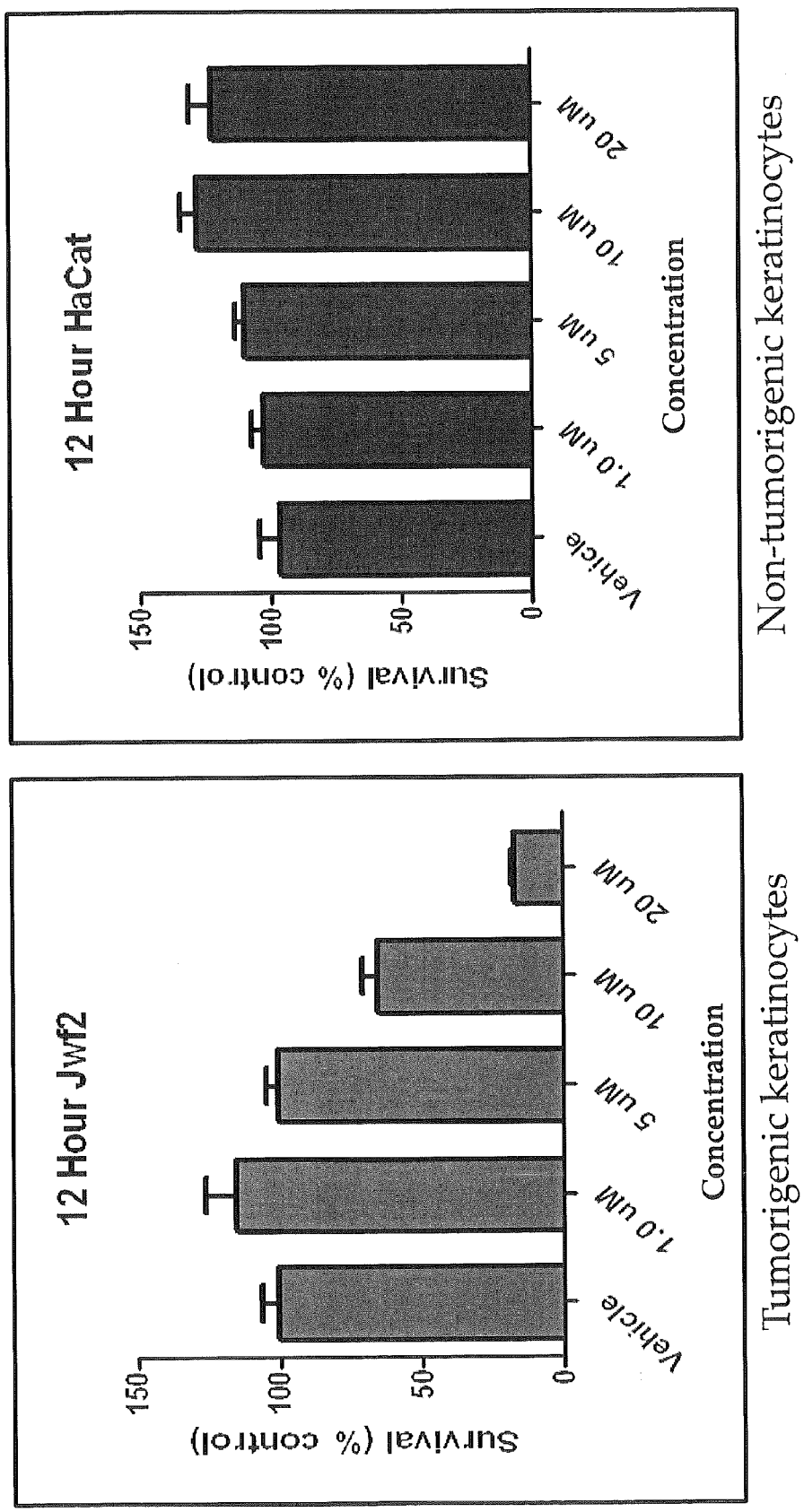
FIG. 15 shows arachidonic acid-derived 15dD12,14-PGJ-EA is selectively toxic in tumor cells.
Figure 16:
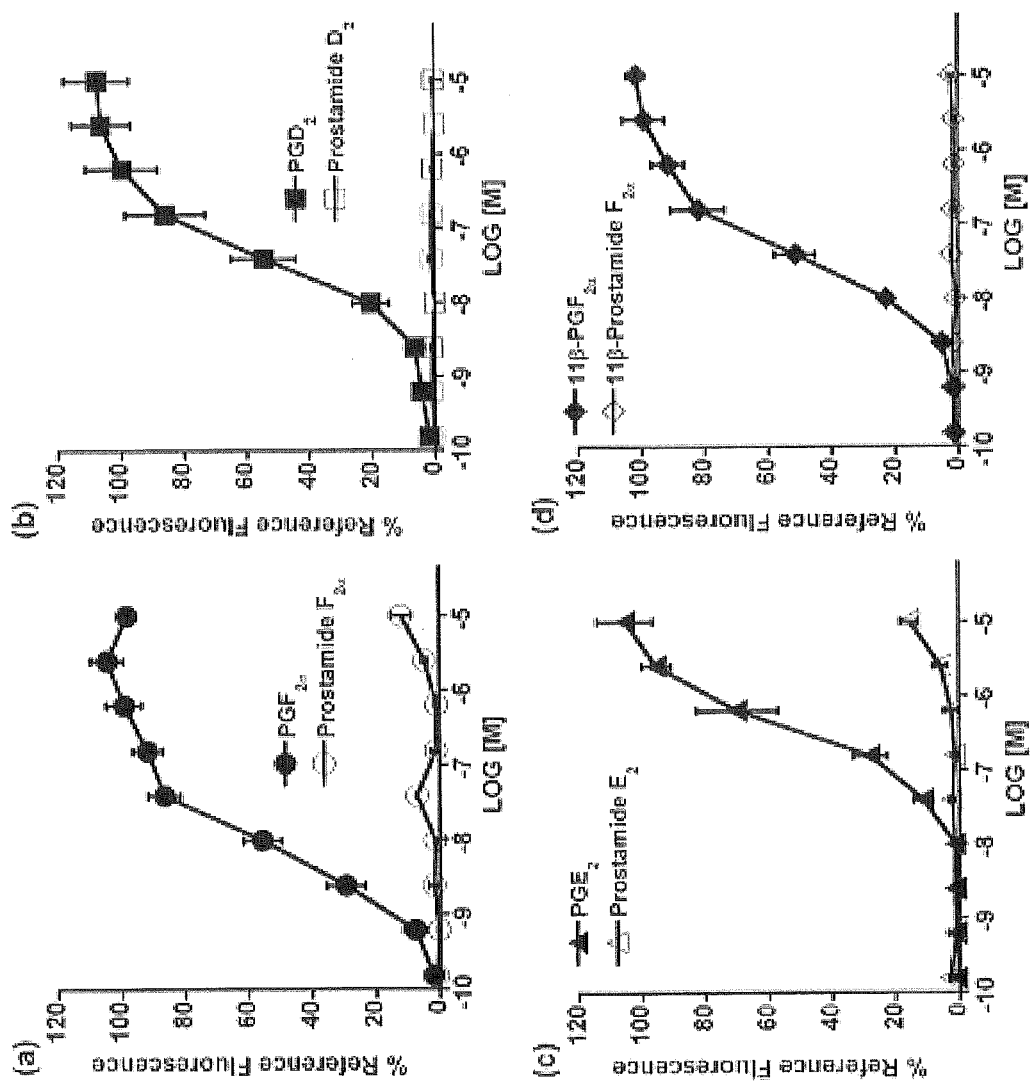
FIG. 16 shows the effect of prostaglandin vs. prostaglandin-EA on Ca$^{2+}$ signaling as determined by fluorescence.
Figure 17:
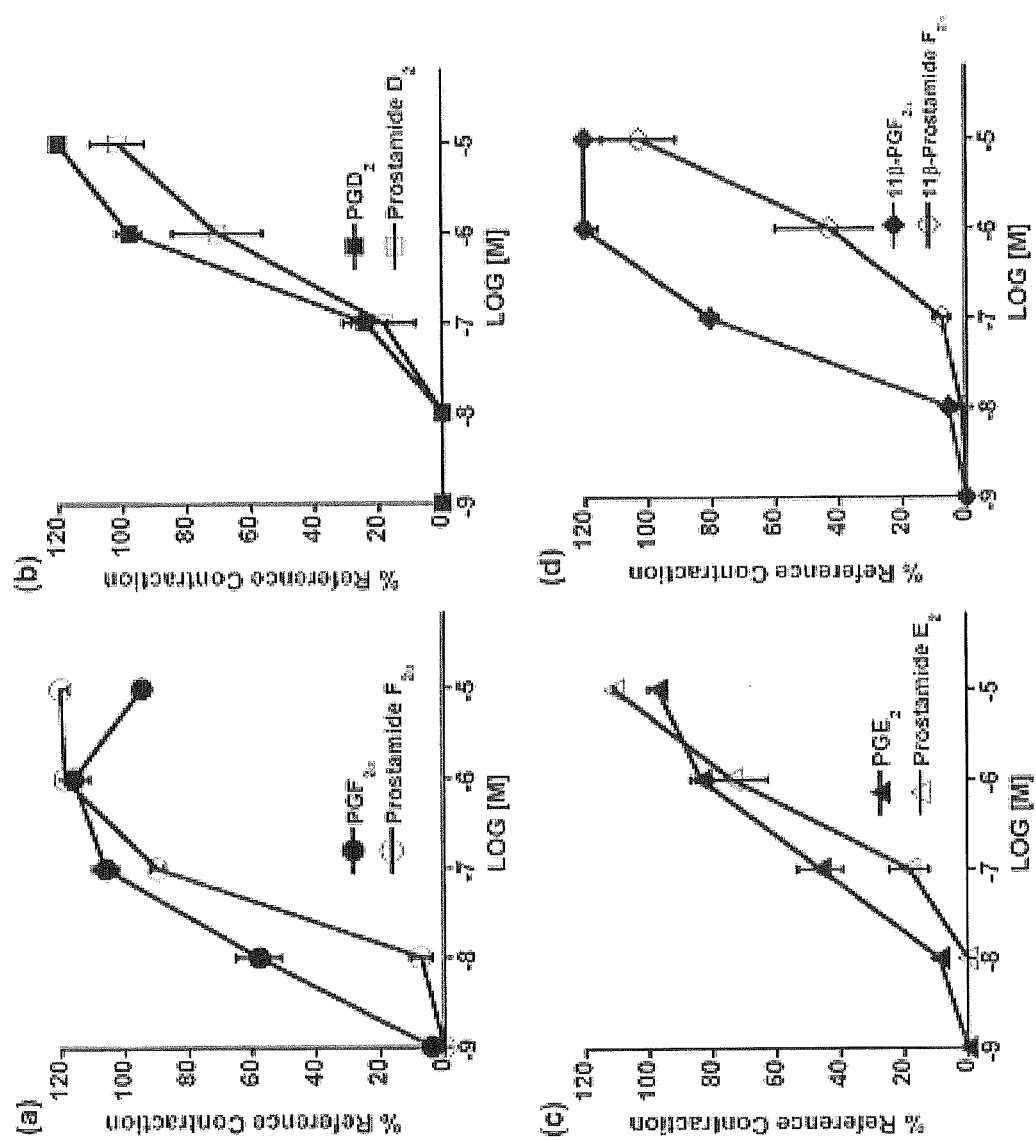
FIG. 17 shows the effect of prostaglandin vs. prostaglandin-EA on Ca$^{2+}$ signaling as determined by % reference contraction.

FIGS. 15 and 16 show the differences between various prostaglandins and prostaglandin-ethanolamides in their effect on Ca$^{2+}$ signaling.

Uses of 15-Deoxy $\Delta^{12,14}$PGJ$_2$-EA and AEA

15dPGJ-EA can be useful for topical treatment of NMSC. NMSC is typically treated with topical 5FU and/or by surgical excision. Although these techniques are effective for eliminating skin cancer they also produce significant damage to the surrounding non-tumor cells. 15d-PGJ-EA can selectively induce cell death in tumor cells due to its ability to cause ER stress apoptosis.

15dPGJ-EA derivatives and analogs that are poorly absorbed from the GI can be used as an agent in the treatment of colon cancer.

Another use for 15dPGJ-EA is for treatment of psoriasis. Psoriasis is characterized by excessive cytokine production to leads to keratinocyte proliferation. Psoriasis is typically treated with topical corticosteroids however prolonged use of these agents is associated with many disorders including atrophy of the skin and loss of effectiveness.

AEA can be used as an agent for skin cancer elimination. AEA may be combined with an enzyme inhibitor of FAAH which blocks AEA degradation.

AEA can be used as an agent for colon cancer treatment. Derivatives and analogs of AEA that have poor absorption properties may be used in the treatment of colon cancer. These molecules will accumulate in the GI and have minimal entry into the systemic circulation to decrease adverse effects.

These molecules can be superior over agents that are currently available due decreased adverse effects and tumor cell selectivity due to the overexpression of COX-2.

The invention claimed is:

1. A compound of formula (I)

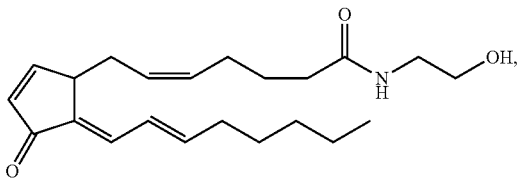

or pharmaceutically acceptable salts thereof.

2. A pharmaceutical composition comprising the compound of claim 1 and a pharmaceutically acceptable carrier.

3. The pharmaceutical composition of claim 2, wherein the pharmaceutical composition is in the form of a powder, emulsion, gel, ointment, dispersion, suspension, cream, foam, aerosol, droplet, an injectable form or coating.

4. A method of treating non-melanoma skin cancer (NMSC) comprising administering an effective amount of the compound of claim 1 to a subject in need thereof.

5. The method of claim 4, wherein the NMSC is a basal cell carcinoma (BCC), squamous cell carcinoma (SCC), Kaposi's sarcoma, a cutaneous lymphoma, a skin adnexal tumor, a sarcoma, a Merkel cell carcinoma, or a combination thereof.

6. The method of claim 4, wherein administration is topical administration.

7. The method of claim 4, wherein administration is transdermal administration.

8. A pharmaceutical composition comprising 15-deoxy $\Delta^{12,14}$-prostagladin $J_2$-ethanolamide, or a pharmaceutically acceptable salt thereof, and a pharmaceutically acceptable carrier.

9. A method of treating a condition comprising administration of an effective amount of 15-deoxy $\Delta^{12,14}$-prostagladin $J_2$-ethanolamide, or a pharmaceutically acceptable salt thereof, to a subject in need thereof, wherein the condition is selected from the group consisting of non-melanoma skin cancer (NMSC), psoriasis, colon cancer, rectal cancer and colorectal cancer.

10. The method of claim 9, wherein the condition is NMSC.

11. The method of claim 9, wherein the condition is colon cancer, rectal cancer or colorectal cancer.

\* \* \* \* \*